(12) United States Patent
Amin et al.

(10) Patent No.: US 6,579,884 B1
(45) Date of Patent: Jun. 17, 2003

(54) COMPOUNDS

(75) Inventors: Kosrat Amin; Mikael Dahlström, both of Mölndal; Peter Nordberg, Sävedalen; Ingemar Starke, Göteborg, all of (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/402,919

(22) PCT Filed: Aug. 18, 1999

(86) PCT No.: PCT/SE99/01402

§ 371 (c)(1),
(2), (4) Date: Oct. 13, 1999

(87) PCT Pub. No.: WO00/11000

PCT Pub. Date: Mar. 2, 2000

(30) Foreign Application Priority Data

Aug. 21, 1998 (SE) .............................................. 9802794

(51) Int. Cl.⁷ ..................... A61K 31/437; C07D 471/04
(52) U.S. Cl. ....................................... 514/300; 546/121
(58) Field of Search ........................... 514/300; 546/121

(56) References Cited

U.S. PATENT DOCUMENTS

| | | | | |
|---|---|---|---|---|
| 4,450,164 A | * | 5/1984 | Bristol et al. | 424/256 |
| 4,725,601 A | * | 2/1988 | Ueda et al. | 514/300 |
| 5,574,042 A | | 11/1996 | Oku et al. | 514/300 |
| 5,665,730 A | | 9/1997 | Senn-Bilfinger et al. | 514/300 |
| 5,719,161 A | | 2/1998 | Rainer | 514/300 |
| 5,824,687 A | | 10/1998 | Senn-Bilfinger | 514/300 |
| 6,096,758 A | | 8/2000 | Grundler et al. | 514/300 |
| 6,124,313 A | | 9/2000 | Grundler et al. | 514/300 |

FOREIGN PATENT DOCUMENTS

| | | |
|---|---|---|
| CA | 2196075 | 2/1996 |
| CA | 2196076 | 2/1996 |
| CA | 2196077 | 2/1996 |
| DE | 19602853 | 7/1997 |
| EP | 0033094 | 8/1981 |
| EP | 0204285 | 12/1986 |
| WO | 9418199 | 8/1994 |
| WO | 9424130 | 10/1994 |
| WO | 9510518 | 4/1995 |
| WO | 9603402 | 2/1996 |
| WO | 9603403 | 2/1996 |
| WO | 9603404 | 2/1996 |
| WO | 9603405 | 2/1996 |
| WO | 9727192 | 7/1997 |

OTHER PUBLICATIONS

Kaminski, J.J. et al.: Antiulcer agents. J. Med. Chem. vol. 28, pp. 876–892, 1985.*
Kaminski, J.J. et al.: Antiulcer agents. J. Med. Chem. vol. 30, pp. 2031–2046, 1987.*
Kaminski, J.J. et al.: Antiulcer agents. J. med. Chem. vol. 32, pp. 1686–1700, 1989.*
Kaminski et al., Journal of Medicinal Chemistry, vol. 28, No. 7, 876–892, 1985.
Kaminski et al., Journal of Medicinal Chemistry, vol. 30, No. 11, 2031–2046, 1987.
Kaminski et al., Journal of Medicinal Chemistry, vol. 30, No. 11, 2047–2051, 1987.
Kaminski et al., Journal of Medicinal Chemistry, vol. 32, No. 8, 1686–1700, 1989.
Kaminski et al., Journal of Medicinal Chemistry, vol. 34, No. 2, 533–541, 1991.

* cited by examiner

Primary Examiner—Charanjit S. Aulakh
(74) Attorney, Agent, or Firm—White & Case LLP

(57) ABSTRACT

The present invention relates to novel compounds, and therapeutically acceptable salts thereof of the formula (I), which inhibit exogenously or endogenously stimulated gastric acid secretion and thus can be used in the prevention and treatment of gastrointestinal inflammatory diseases.

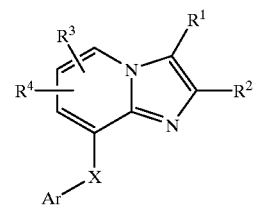

17 Claims, No Drawings

COMPOUNDS

TECHNICAL FIELD

This application is a 371 of PCT/SE99/01402 filed Aug. 18, 1999 now WO 00/11000 Mar. 2, 2000.

The present invention relates to novel compounds, and therapeutically acceptable salts thereof, which inhibit exogenously or endogenously stimulated gastric acid secretion and thus can be used in the prevention and treatment of gastrointestinal inflammatory diseases. In further aspects, the invention relates to compounds of the invention for use in therapy; to processes for preparation of such new compounds; to pharmaceutical compositions containing at least one compound of the invention, or a therapeutically acceptable salt thereof, as active ingredient; and to the use of the active compounds in the manufacture of medicaments for the medical use indicated above.

BACKGROUND ART

Substituted imidazo[1,2-a]pyridines, useful in the treatment of peptic ulcer diseases, are known in the art, e.g. from EP-B-0033094 and U.S. Pat. No. 4,450,164 (Schering Corporation); from EP-B-0204285 and U.S. Pat. No. 4,725,601 (Fujisawa Pharmaceutical Co.); from WO 9418199 and WO 9510518 (Byk Gulden Lomberg Chem.) and from publications by J. J. Kaminski et al. in the Journal of Medical Chemistry (vol. 28, 876–892, 1985; vol. 30, 2031–2046, 1987; vol. 30, 2047–2051, 1987; vol. 32, 1686–1700, 1989; and vol. 34, 533–541, 1991).

For a review of the pharmacology of the gastric acid pump (the $H^+$, $K^+$-ATPase), see Sachs et al. (1995) Annu. Rev. Pharmacol. Toxicol. 35: 277–305.

DISCLOSURE OF THE INVENTION

It has surprisingly been found that compounds of the Formula I, which are substituted imidazopyridine derivatives, are effective as inhibitors of the gastrointestinal $H^+$, $K^+$-ATPase and thereby as inhibitors of gastric acid secretion.

In one aspect, the invention thus relates to compounds of the general Formula I:

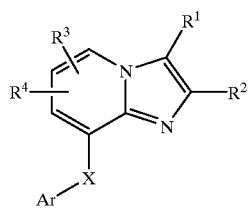

or a pharmaceutically acceptable salt thereof, wherein $R^1$ is
(a) H,
(b) $C_1$–$C_6$ alkyl,
(c) $C_1$–$C_6$ alkenyl,
(d) $CH_2OH$,
(e) halogen, or
(f) thiocyano $R^2$ is
(a) $C_1$–$C_6$ alkyl,
(b) hydroxyalkyl,
(c) $C_1$–$C_6$ alkoxy $C_1$–$C_6$ alkyl,
(d) hydroxy $C_1$–$C_6$ alkoxy $C_1$–$C_6$ alkyl,
(e) $C_1$–$C_6$ alkylthio $C_1$–$C_6$ alkyl,
(f) cyano $C_1$–$C_6$ alkyl,
(g) halogenated $C_1$–$C_6$ alkyl, or
(h) aminocarbonyl $C_1$–$C_6$ alkyl $R^3$ is
(a) H,
(b) $C_1$–$C_6$ alkoxy,
(c) $C_1$–$C_6$ alkyl,
(d) halogen,
(e) hydroxy $C_1$–$C_6$ alkyl.
(f) hydroxy $C_1$–$C_6$ alkoxy,
(g) $C_1$–$C_6$ alkoxy $C_1$–$C_6$ alkyl,
(h) $C_1$–$C_6$ alkoxy $C_1$–$C_6$ alkoxy,
(i) $C_1$–$C_6$ alkoxycarbonyl,
(j) $C_1$–$C_6$ alkanoyl,
(k) halogenated $C_1$–$C_6$ alkyl,
(l) $NO_2$,
(m) CN,
(n) $C_1$–$C_6$ sulfonyl,
(o) $C_1$–$C_6$ sulfinyl,
(p) $C_1$–$C_6$ alkylthio,
(q) $C_1$–$C_6$ alkylaminosulfonyl,
(r) $C_1$–$C_6$ (alkyl)$_2$aminosulfonyl,
(s) aminosulfonyl,
(t) $C_1$–$C_6$ alkylsulfonylamino,
(u) $C_1$–$C_6$ (alkylsulfonyl)$_2$amino,
(v) trifluoromethylsulfonylamino,
(x) $C_1$–$C_6$ alkylcarbonylamino,
(y) $C_1$–$C_6$ alkoxycarbonylamino, or
(Z) $C_1$–$C_6$ aminocarbonylamino, optionally substituted by one or two $C_1$–$C_6$ alkyl groups, $R^4$ is
(a) H,
(b) $C_1$–$C_6$ alkyl,
(c) halogenated $C_1$–$C_6$ alkyl,
(d) $C_1$–$C_6$ alkoxy, or
(e) halogen.

Ar is a phenyl, thienyl, furanyl, naphthyl, or pyridyl group substituted with one or more substituents selected from the group consisting of $R^5$, $R^6$, and $R^7$.

X is

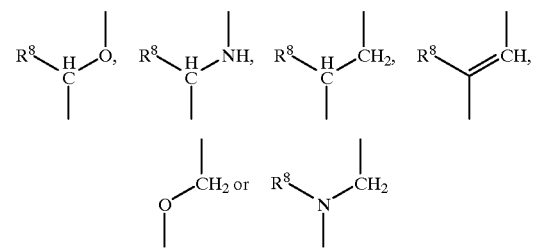

$R^5$ is
(a) H,
(b) $C_1$–$C_6$ alkyl,
(c) $C_1$–$C_6$ alkoxy,
(d) hydroxy,
(e) hydroxy $C_1$–$C_6$ alkyl,
(f) hydroxy $C_1$–$C_6$ alkoxy,
(g) halogenated $C_1$–$C_6$ alkyl,
(h) halogenated $C_1$–$C_6$ alkoxy,
(i) $C_1$–$C_6$ alkoxy $C_1$–$C_6$ alkyl,
() halogen,
(k) hydroxy $C_1$–$C_6$ alkoxy $C_1$–$C_6$ alkyl,
(l) CN, (m) $C_1$–$C_6$ alkoxycarbonyl,
(n) $C_1$–$C_6$ alkoxycarbonyloxy,
(O) $C_1$–$C_6$ alkylsulfonyloxy,
(p) trifluoromethylsulfonyloxy,
(q) $C_1$–$C_6$ acyloxy $C_1$–$C_6$ alkyl,
(r) $C_1$–$C_6$ alkylsulfonyl $C_1$–$C_6$ alkyl.
(s) $C_1$–$C_6$ alkylsulfinyl $C_1$–$C_6$ alkyl,
(t) $C_1$–$C_6$ alkylthio $C_1$–$C_6$ alkyl,
(u) $C_1$–$C_6$ alkoxycarbonylamino $C_1$–$C_6$ alkyl,
(v) aryl,
(x) amino $C_1$–$C_6$ alkyl,
(y) NHC=$OR^{12}$
(z) H or $C_1$–$C_4$ alkyl substituted

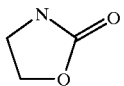

-group
(aa) H or $C_1$–$C_4$ alkyl substituted

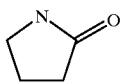

-group, or
(ab) $C_1$–$C_6$ alkyl sulfonyl amino
$R^6$ is
  (a) H,
  (b) $C_1$–$C_6$ alkyl,
  (c) halogen,
  (d) hydroxy $C_1$–$C_6$ alkyl,
  (e) halogenated $C_1$–$C_6$ alkyl,
  (f) halogenated $C_1$–$C_6$ alkoxy,
  (e) $C_1$–$C_6$ alkoxy $C_1$–$C_6$ alkyl, or
  (f) CN
$R^7$ is
  (a) H,
  (b) $C_1$–$C_6$ alkyl,
  (c) $C_1$–$C_6$ alkoxy,
  (d) halogen,
  (e) $NO_2$,
  (f) halogenated $C_1$–$C_6$ alkyl,
  (g) halogenated $C_1$–$C_6$ alkoxy,
  (h) aryloxy, or
  (i) CN
$R^8$ is
  (a) H or
  (b) $C_1$–$C_6$ alkyl $R^{12}$ is
  (a) $C_1$–$C_6$ alkoxy,
  (b) $C_1$–$C_6$ alkoxy $C_1$–$C_4$ alkoxy,
  (c) $NH_2$,
  (d) hydroxy $C_2$–$C_4$ alkoxy,
  (e) $C_1$–$C_6$ alkyl carbonyloxy $C_2$–$C_4$ alkoxy,
  (f) halogenated $C_2$–$C_4$ alkoxy,
  (g) halogenated $C_1$–$C_4$ alkyl,
  (h) hydroxy $C_1$–$C_4$ alkyl,
  (i) $C_1$–$C_6$ alkyl carbonyloxy $C_1$–$C_4$ alkyl,
  (j) aryl,
  (k) aryl $C_1$–$C_4$ alkyl,
  (l) $C_1$–$C_4$ sulfanyl $C_2$–$C_4$ alkoxy,
  (m) $C_1$–$C_4$ sulfinyl $C_2$–$C_4$ alkoxy, or
  (n) $C_1$–$C_4$ sulfonyl $C_2$–$C_4$ alkoxy,
$R^5$ and $R^6$ are in the ortho positions relative to X
$R^7$ is in the meta or para position relative to X $R^5$ and $R^8$ may together form a hydroxy- or alkoxy-substituted 5- or 6-membered ring,
provided that one of $R^3$ and $R^4 \neq H$ or halogen
provided also that at least one of $R^5$, $R^6$ and $R^7 \neq H$
provided also that when $R^5$=(y),(z),(aa) or (ab), at least one of $R^3$ and $R^4 \neq H$
provided also that when $R^1$=H or Cl, XAr≠$OCH_2Ar$
provided also that when $R^1$=H, halogen or $CH_2OH$, at least one of $R^5$ and $R^6$ is $C_1$–$C_6$ alkyl
provided also that when $R^2$ is $CH_2OH$ or $CH_2CN$, at least one of $R^5$ and $R^6$ is $C_1$–$C_6$ alkyl The term "aryl" includes phenyl, naphthyl, thienyl, furyl, pyridyl or imidazolyl, optionally substituents by 1–3 substituents selected from H, $C_1$–$C_6$ alkyl, $C_1$–$C_6$ alkoxy, halogen or $CF_3$.

As used herein, the term "$C_1$–$C_6$ alkyl" denotes a straight or branched alkyl group having from 1 to 6 carbon atoms. Examples of $C_1$–$C_6$ alkyl include methyl, ethyl, n-propyl, iso-propyl, n-butyl, iso-butyl, sec-butyl, t-butyl and straight- and branched-chain pentyl and hexyl.

The term "halogen" includes fluoro, chloro, bromo and iodo.

The term "pyridyl" includes the 2-, 3-, and 4-isomers and the terms thienyl and furanyl include the 2-, and 3-isomers.

Both the pure enantiomers, racemic mixtures and unequal mixtures of the two enantiomers are within the scope of the invention. It should be understood that all the possible diastereomeric forms (pure enantiomers, racemic mixtures and unequal mixtures of two enantiomers) are within the scope of the present invention. Also included in the invention are derivatives of the compounds of the Formula I which have the biological function of the compounds of the Formula I.

Depending on the process conditions the end products of the Formula I are obtained either in neutral or salt form. Both the free base and the salts of these end products are within the scope of the present invention.

Acid addition salts of the new compounds may in a manner known per se be transformed into the free base using basic agents such as alkali or by ion exchange. The free base obtained may also form salts with organic or inorganic acids.

In the preparation of acid addition salts, preferably such acids are used which form suitable therapeutically acceptable salts. Examples of such acids are hydrohalogen acids such as hydrochloric acid, sulfuric acid, phosphoric acid, nitric acid, aliphatic, alicyclic, aromatic or heterocyclic carboxylic or sulfonic acids, such as formic acid, acetic acid, propionic acid, succinic acid, glycolic acid, lactic acid, malic acid, tartaric acid, citric acid, ascorbic acid, maleic acid, hydroxymaleic acid, pyruvic acid, p-hydroxybensoic acid, embonic acid, methanesulfonic acid, ethanesulfonic acid, hydroxyethanesulfonic acid, halogenbensenesulfonic acid, toluenesulfonic acid or naphthalenesulfonic acid.

Preferred compounds according to the invention are those of the formula I wherein
$R^1$ is H, $CH_3$, $CH_2OH$;
$R^2$ is $CH_3$, $CH_2CH_3$, $CH_2CH_2OH$, $CH_2CH_2SCH_3$, $CH_2CH_2OCH_3$ or $CH_2CH_2CN$;
$R^3$ is H, $CH_3$, $CH_2CH_3$, F, Cl, Br, $OCH_3$,$OCH_2CH_3$, $CH_2OH$, $CH_2CH_2OH$, $OCH_2CH_2OH$, $CH_2CH_2OCH_3$, $OCH_2CH_2OCH_3$, C=$OOCH_3$, C=$OOCH_2CH_3$ C=$OCH_3$, C=$OCH_2CH_3$, C=$OCH(CH_3)_2$, or C=$OCH_2CH_2CH_3$,
$R^4$ is H, $CH_3$, $CH_2CH_3$, F, Cl, Br, $OCH_3$ or $OCH_2CH_3$;

Ar is phenyl, thienyl, furyl naphthyl;

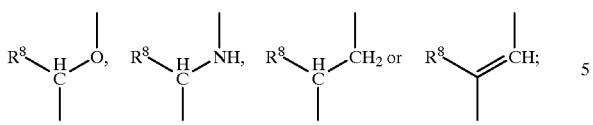

$R^5$ is H, $CH_3$, $CH_2CH_3$, $OCH_3$, OH, $CH_2OH$, $CH_2OCH_3$, $CH_2CH_2OH$, $CH_2CH_2OCH_3$, $OCH_2CH_2OH$, $OC=OOCH_3$, $OC=OCH_2CH_3$, $OCHF_2$, $OCF_3$, F, Cl, Br, CN, phenyl, $CH_2CH_2OC=OCH_3$, $CH_2NHC=OOCH_3$ or $CH_2NHC=OOCH_2CH_3$;

$R^6$ is H, $CH_3$, $CH_2CH_3$, $CF_3$, $OCF_3$, $OCF_2H$, F, Cl, Br, or $CH_2OCH_3$;

$R^7$ is H, F, Cl Br, $OCF_2H$, or $OCF_3$;

$R^8$ is H or $CH_3$, or $CH_2CH_3$.

More preferred compounds according to the invention are those of the formula I wherein $R^1$ is H, $CH_3$ or $CH_2OH$;

$R^2$ is $CH_3$, $CH_2CH_3$, $CH_2OH$, $CH_2SCH_3$, $CH_2OCH_3$ or $CH_2CN$;

$R^3$ is H, $CH_3$, $CH_2CH_3$, $OCH_3$, $OCH_3$, $CH_2OH$, $C=OCH_2CH$; $C=OOCH_2CH_3$, $C=OCH_3$, $C=OCH_2CH_3$, or $C=OCH_2CH_2CH_3$;

$R^4$ is H, or $CH_3$;

Ar is phenyl, thienyl or furyl

X is

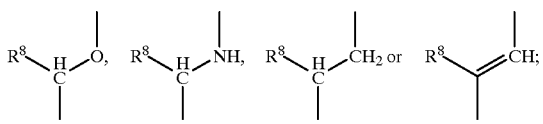

$R^5$ is H, $CH_3$, $CH_2CH_3$, $OCH_3$, OH, $CH_2OH$, $CH_2OCH_3$, $CH_2CH_2OH$, $CH_2CH_2OCH_3$, $OCH_2CH_2OH$, $OC=OOCH_3$, $OC=OCH_2CH_3$, $OCHF_2$, $OCF_3$, F, Cl, Br, CN, $CH_2CH_2OC=OCH_3$, $CH_2NHC=OOCH_3$ or $CH_2NHC=OOCH_2CH_3$ $R^6$ is H, $CH_3$, $CH_2CH_3$, $CF_3$, $OCF_3$, $OCF_2H$, F, Cl, Br or $CH_2OCH_3$;

$R^7$ is H, F, Cl, Br, $OCF_2H$, $OCF_3$;

$R^8$ is H or $CH_3$.

Preparation

The present invention also provides the following processes A, B, C, D or E for the manufacture of compounds with the general Formula I.

Process A

Process A for manufacture of compounds with the general Formula I comprises the following steps:

Compounds of the general Formula II (II)

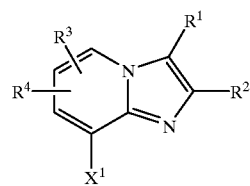

wherein $X^1$ is $NH_2$ or OH, and $R^1$, $R^2$, $R^3$, and $R^4$ are as defined for Formula I, can be reacted with compounds of the general Formula III (III)

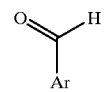

wherein "Ar" is as defined for Formula I and Y is a leaving group, such as a halide, tosyloxy or mesyloxy, to the compounds of the Formula I.

It is convenient to conduct this reaction in an inert solvent, e.g. acetone, acetonitrile, dimethoxyethane, methanol, ethanol or dimethylformamide with or without a base. The base is e.g. an alkali metal hydroxide, such as sodium hydroxide and potassium hydroxide; an alkali metal carbonate, such as potassium carbonate and sodium carbonate; or an organic amine, such as triethylamine Process B Process B for manufacture of compounds with the general Formula I, wherein X is NH, comprises the following steps:

Compounds of the general Formula IV (IV)

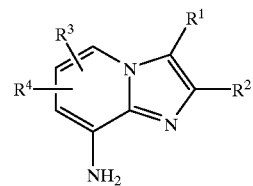

wherein $R^1$, $R^2$, $R^3$ and $R^4$ are as defined for Formula I, can be reacted with compounds of the general Formula V (V)

O=C(H)(Ar)

wherein "Ar" are as defined for Formula I, in the presence of a Lewis acid e.g. zinc chloride to the compounds of the Formula VI (VI)

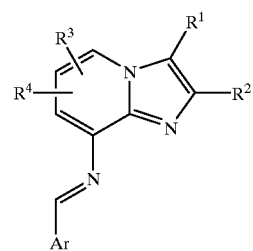

wherein $R^1$, $R^2$, $R^3$, $R^4$ and Ar are as defined for Formula I, whereupon the compounds of the general Formula VI are reduced e.g. by using sodium borohydride or sodiumcyano borohydride to compounds of the general Formula I, wherein X is NH. The reactions can be carried out under standard conditions in an inert solvent e.g. methanol or ethanol.

Process C

Process C for manufacture of compounds with the general Formula I, wherein $R^1$ is $CH_2OH$ or H comprises the following steps:

Compounds of the general Formula VII

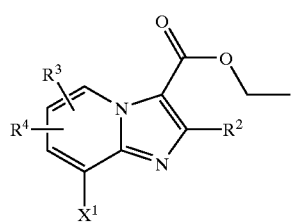

(VII)

wherein $X^1$ is $NH_2$ or OH, and $R^2$, $R^3$ and $R^4$ are as defined for Formula I, can be reacted with compounds of the general Formula III

(III)

wherein Ar is as defined for Formula I and Y is a leaving group, such as a halide, tosyloxy or mesyloxy, to the compounds of the Formula VIII

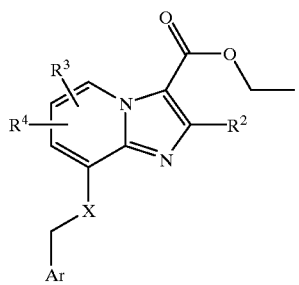

(VIII)

wherein $R^2$, $R^3$, $R^4$, Ar and X are as defined for Formula I.

It is convenient to conduct this reaction in an inert solvent, e.g. acetone, acetonitrile, dimethoxyethane, methanol, ethanol or N,N-dimethylformamide with or without a base. The base is e.g. an alkali metal hydroxide, such as sodium hydroxide and potassium hydroxide; an alkali metal carbonate, such as potassium carbonate and sodium carbonate, or an organic amine, such as triethylamine.

Reduction of compounds of the general Formula VIII, e.g. by using lithium aluminum hydride in tetrahydrofuran or ether yields the compounds of the general Formula I wherein $R^1$ is $CH_2OH$.

Hydrolysis of compounds of formula VIII, e.g. by using a base such as sodium hydroxide or an acid such as hydrochloric acid. After hydrolysis, decarboxylation in an inert solvent such as diphenylether gives the compounds of formula I wherein $R^1$ is H.

Process D

Process D for manufacture of compounds with the general Formula I, wherein $R^1$ is H or $CH_2OH$ and X is NH comprises the following steps:

Compounds of the Formula IX

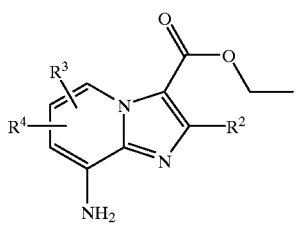

(IX)

$R^2$, $R^3$, and $R^4$ are as defined for Formula I, can be reacted with compounds of the general Formula V

(V)

wherein Ar is as defined for Formula I, in the presence of a Lewis acid, e.g. zinc chloride to the compounds of the Formula X

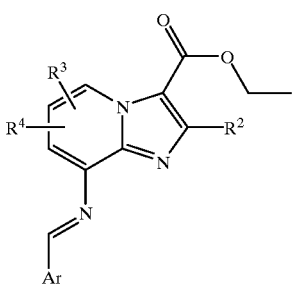

(X)

wherein $R^2$, $R^3$, $R^4$ and Ar are as defined for Formula I, whereupon the compounds of the general Formula X are reduced, e.g. by using sodium borohydride or sodium cyano borohydride to compounds of the general Formula XI

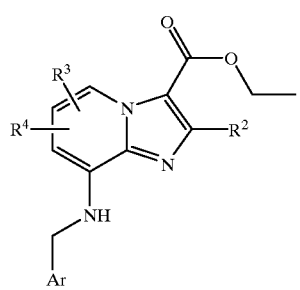

(XI)

wherein $R^2$, $R^3$, $R^4$ and Ar are as defined for Formula I. The reactions can be carried out under standard conditions in an inert solvent e.g. methanol or ethanol.

Reduction of compounds of the general Formula XI e.g. by using lithium aluminium hydride in tetrahydrofuran or ether yields the compounds of the general Formula I wherein $R^1$ is $CH_2OH$ and X is NH.

Hydrolysis of compounds of formula XI, e.g. by using a base such as sodium hydroxide or an acid such as hydrochloric acid. After hydrolysis, decarboxylation in an inert solvent such as diphenylether gives the compounds of formula I wherein $R^1$ is H.

Process E

Condensation of compounds of the general Formula XII (XII)

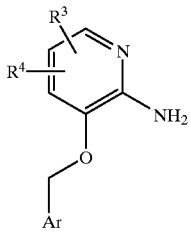

wherein $R^3$, $R^4$, and Ar are as defined for Formula I, with (α-halocarbonyl intermediates of the general formula $R^2COCH(Z)R^1$ wherein Z is a leaving group such as Br or Cl, in an inert solvent e.g. acetonitrile or ethanol results in formation of compounds of the general Formula XIII wherein $R^2$, $R^3$, $R^4$, and Ar are as defined for Formula I (XIII)

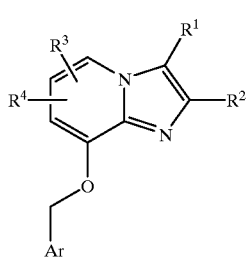

Medical Use

In a further aspect, the invention relates to compounds of the formula I for use in therapy, in particular for use against gastrointestinal inflammatory diseases. The invention also provides the use of a compound of the formula I in the manufacture of a medicament for the inhibition of gastric acid secretion, or for the treatment of gastrointestinal inflammatory diseases.

The compounds according to the invention may thus be used for prevention and treatment of gastrointestinal inflammatory diseases, and gastric acid-related diseases in mammals including man, such as gastritis, gastric ulcer, duodenal ulcer, reflux esophagitis and Zollinger-Ellison syndrome. Furthermore, the compounds may be used for treatment of other gastrointestinal disorders where gastric antisecretory effect is desirable, e.g. in patients with gastrinomas, and in patients with acute upper gastrointestinal bleeding. They may also be used in patients in intensive care situations, and pre-and postoperatively to prevent acid aspiration and stress ulceration.

The typical daily dose of the active substance varies within a wide range and will depend on various factors such as for example the individual requirement of each patient, the route of administration and the disease. In general, oral and parenteral dosages will be in the range of 5 to 1000 mg per day of active substance.

Pharmaceutical Formulations

In yet a further aspect, the invention relates to pharmaceutical compositions containing at least one compound of the invention, or a therapeutically acceptable salt thereof, as active ingredient.

The compounds of the invention can also be used in formulations together with other active ingredients, e.g. antibiotics, such as amoxicillin.

For clinical use, the compounds of the invention are formulated into pharmaceutical formulations for oral, rectal, parenteral or other mode of administration. The pharmaceutical formulation contains a compound of the invention in combination with one or more pharmaceutically acceptable ingredients. The carrier may be in the form of a solid, semi-solid or liquid diluent, or a capsule. These pharmaceutical preparations are a further object of the invention. Usually the amount of active compounds is between 0.1–95% by weight of the preparation, preferably between 0.1–20% by weight in preparations for parenteral use and preferably between 0.1 and 50% by weight in preparations for oral administration.

In the preparation of pharmaceutical formulations containing a compound of the present invention in the form of dosage units for oral administration the compound selected may be mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

Soft gelatin capsules may be prepared with capsules containing a mixture of the active compound or compounds of the invention, vegetable oil, fat, or other suitable vehicle for soft gelatin capsules. Hard gelatin capsules may contain granules of the active compound. Hard gelatin capsules may also contain the active compound in combination with solid powdered ingredients such as lactose, saccharose, sorbitol, mannitol, potato starch, corn starch, amylopectin, cellulose derivatives or gelatin.

Dosage units for rectal administration may be prepared (i) in the form of suppositories which contain the active substance mixed with a neutral fat base; (ii) in the form of a gelatin rectal capsule which contains the active substance in a mixture with a vegetable oil, paraffin oil or other suitable vehicle for gelatin rectal capsules; (iii) in the form of a ready-made micro enema; or (iv) in the form of a dry micro enema formulation to be reconstituted in a suitable solvent just prior to administration.

Liquid preparations for oral administration may be prepared in the form of syrups or suspensions, e.g. solutions or suspensions containing from 0.1% to 20% by weight of the active ingredient and the remainder consisting of sugar or sugar alcohols and a mixture of ethanol, water, glycerol, propylene glycol and polyethylene glycol. If desired, such liquid preparations may contain coloring agents, flavoring agents, saccharine and carboxymethyl cellulose or other thickening agent. Liquid preparations for oral administration may also be prepared in the form of a dry powder to be reconstituted with a suitable solvent prior to use.

Solutions for parenteral administration may be prepared as a solution of a compound of the invention in a pharmaceutically acceptable solvent, preferably in a concentration from 0.1% to 10% by weight. These solutions may also contain stabilizing ingredients and/or buffering ingredients and are dispensed into unit doses in the form of ampoules or vials. Solutions for parenteral administration may also be prepared as a dry preparation to be reconstituted with a suitable solvent extemporaneously before use.

The compounds according to the invention can also be used in formulations together with other active ingredients, e.g. for the treatment or prophylaxis of conditions involving infection by *Helicobacter pylori* of human gastric mucosa. Such other active ingredients may be antimicrobial agents, in particular:

- β-lactam antibiotics such as amoxicillin, ampicillin, cephalothin, cefaclor or cefixime;
- macrolides such as erythromycin, or clarithromycin,
- tetracyclines such as tetracycline or doxycycline;
- aminoglycosides such as gentamycin, kanamycin or amikacin;
- quinolones such as norfloxacin, ciprofloxacin or enoxacin;
- others such as metronidazole, nitrofurantoin or chloramphenicol; or
- preparations containing bismuth salts such as bismuth subcitrate, bismuth subsalicylate, bismuth subcarbonate, bismuth subnitrate or bismuth subgallate.

Examples

EXAMPLES

1. Preparation of Compounds of the Invention

Example 1.1

Synthesis of 2,3-dimethyl-8-(2,6-dimethylbenzylamino)-6-methoxyimidazo[1,2-a]pyridine A mixture of 8-amino-6-methoxy-2,3-imidazo[1,2-a]pyridine (0.4 g, 2.09 mmol), 2,6-dimethylbenzylchloride (0.32 g, 2.07 mmol), sodium carbonate (0.4 g), potassium iodide (0.2 g) and acetonitrile (5 ml) was refluxed for 5 hours. The solvent was evaporated and the residue was purified by chromatography (methylene chloride:ethyl acetate, 70:30) yielding 250 mg (39%) of the desired product.

Example 1.2–1.6, 1.9–1.16, 1.18–1.28, 1.30–1.40, 1.48–1.50 and 1.78–1.79 were prepared according to example 1.

Example 1.2

Synthesis of 2,3-dimethyl-8-(2,6-dimethylbenzylamino)-6-nitroimidazo[1,2-a]pyridine Yield: 86%

$^1$H-NMR (300 MHz, CDCl$_3$): δ2.3 (s, 3H), 2.35 (s, 6H), 2.45 (s, 3H), 4.4 (d, 2H), 5.05 (bs, 1H), 6.9 (s, 1H), 7.05–7.15 (m, 3H), 8.4 (s, 1H)

Example 1.3

Synthesis of 2,3-dimethyl-8-(2,6-dimethylbenzylamino)-6-trifluoromethylimidazo[1,2-a]pyridine Yield: 81%

$^1$H-NMR (300 MHz, CDCl$_3$): δ2.35 (s, 3H), 2.38 (s, 6H), 2.4 (s, 3H), 4.3 (d, 2H), 495 (bs, 1H), 6.25 (s, 1H), 6.75 (d, 2H), 7.6 (s, 1H)

Example 1.4

Synthesis of 8-(2,6-dimethylbenzylamino)-2,3,5-trimethylimidazo[1,2-a]pyridine

Yield: 52%

$^1$H-NMR (300 MHz, CDCl$_3$): δ2.3 (s, 3H), 2.4 (6H), 2.65 (s, 3H), 2.75 (s, 3H), 4.3 (d, 2H), 4.65 (bs, 1H), 6.05 (d, 1H), 6.3 (d, 1H) 6.95–7.15 (m, 3H)

Example 1.5

Synthesis of 8-(2-methylbenylamino)-2,3,6-trimethylimidazo[1,2-a]pyridine

Yield: 60%

$^1$H-NMR (300 MHz, CDCl$_3$): δ2.25 (s, 3H), 3.32 (s, 3H), 2.36 (s, 3H), 2.38 (s, 3H), 4.38 (d,2H), 5.20 (t, 1H), 5.93 (s, 1H), 7.02 (s, 1H), 7.17–7.33 (m, 4H)

Example 1.6

Synthesis of ethyl 8-(2,6-dimethylbenzylamino) -2, 3-dimethylimidazo[1,2-a]pyridine-6-carboxylate Yield: 37%

$^1$H-NMR (300 MHz, CDCl$_3$): δ1.45 (t, 3H), 2.35 (s, 3H), 2.4 (s, 6H), 2.45 (s, 3H), 4.4–4.5 (m, 4H), 4.85 (bs, 1H), 6.75 (s, 1H), 7.05–7.15 (m, 3H), 8.05 (s, 1H)

Example 1.7

Synthesis of 8-(4-methoxy-2,6-dimethylbenzylamino)-2,3-dimethylimidazo[1,2-a]pyridine 8-amino-2,3-dimethylimidazo[1,2-a]pyridine (0.5 g, 3.1 mmol), 4-methoxy-2.6-dimethylbenzaldehyd (0.51 g, 3.11 mmol) were dissolved in methanol (10 ml) whereupon zinc chloride (0.51 g, 3.82 mmol) dissolved in methanol (5 ml) was added. Sodium cyanoborohydride was added in portions and the mixture was refluxed for 3 h under under nitrogen. The mixture was stirred at 0–5° C. and 1 M sodium hydroxide (20 ml) was added. After extraction with 2×50 ml of methylene chloride the combined organic layer was washed with water and dried over sodium sulfate. The solvent was removed under reduced pressure. The residue was chromatographed on silica (dichloromethane: ethyl acetate. 1:1) yielding 0.58 g 60% of the title compound.

$^1$H-NMR (300 MHz, CDCl$_3$): δ2.35 (s, 12H), 3.79 (s, 3H), 4.27 (d, 2H), 4.75 (t, 1H), 6.19 (d, 1H), 6.59 (s, 2H), 6.69–6.75 (m, 1H), 7.24 (d, 1H)

Example 1.8, 1.17 and 1.41–1.45 were prepared according to Example 7.

Example 1.8

Synthesis of8-[(2,6-bismethoxymethyl) benzylamino)]-2,3,6-trimethylimidazo[1,2-a]pyridine Yield: 54%

$^1$H-NMR (300 MHz, CDCl$_3$): δ2.25 (s, 3H), 2.3 (s, 6H), 3.35 (s, 6H), 4.45 (d, 2H), 4.5 (s, 4H), 4.95 (bs, 1H), 6.15 (s, 1H), 7.0 (s, 1H), 7.2–7.35(m, 3H)

Example 1.9–1.28 were prepared according to Example 1.1

Example 1.9

Synthesis of 8-(2,6-dimethylbenzylamino)-3-fluoro-2-methylimidazo[1,2-a]pyridine Yield: 33%

$^1$H-NMR (300 MHz, CDCl$_3$): δ2.3 (s,3H), 2.35 (s, 6H), 4.3 (d, 2H), 4.8 (bs, 1H), 6.15 (d, 1H), 6.7 (t, 1H), 6.95–7.15 (m, 3H), 7.25 (d, 1H)

Example 1.10

Synthesis of 3-chloro-8-(2,6-dimethylbenzylamino)
-2-methylimidazo[1,2-a]pyridine Yield: 0.6%

$^1$H-NMR (300 MHz, CDCl$_3$): δ2.4 (s, 6H), 2.45 (s, 3H), 4.35 (d, 2H), 4.8 (bs, 1H), 6.3 (d, 1H), 6.8 (t, 1H), 7.05–7.15 (m, 3H), 7.5 (d, 1H)

Example 1.11

Synthesis of 2,3-dimethyl-8-(2-phenylbenzylamino)-imidazo[1,2-a]pyridine

Yield: 15%

$^1$H-NMR (300 MHz, CDCl$_3$): δ2.35 (s, 3H), 2.4 (s, 3H), 4.35 (d, 2H), 5.35 (t, 1H), 5.85 (d, 1H) 6.55 (t, 1H), 7.20 (d, 1H), 7.25–7.4 (m, 8H), 7.55 (m, 1H)

Example 1.12

Synthesis of 2,3-dimethyl-8-[(2,4-dimethyl-3-furyl)methylamino]-imidazo[1,2-a]pyridine Yield: 4%

$^1$H-NMR (300 MHz, CDCl$_3$): δ1.95 (s, 3H), 2,25 (s, 3H), 2.35 (s, 3H), 2.4 (s, 3H), 4.1 (d, 2H), 4.9 (bs, 1H), 6.15 (d, 1H), 6.7 (t, 1H), 7.05 (s, 1H), 7.25 (d, 1H)

Example 1.13

Synthesis of 2,3-dimethyl-8-[(2-methyl-1-naphtyl)methylamino]-imidazo[1,2-a]pyridine hydrochloride Yield: 24%

$^1$H-NMR (300 MHz, DMSO): δ2.35 (s, 3H), 2.45 (s, 3H), 2.6 (s, 3H), 4.8 (d, 2H), 6.6 (bs, 1H), 7.15 (d, 1H), 7.35–7.55 (m, 4H), 7.8–8.1 (m, 4H)

Example 1.14

Synthesis of 8-[(1-bromo-2-naphtyl)methylamino]-2, 3 -dimethylimidazo [1,2-a]pyridine Yield: 21%

$^1$H-NMR (300 MHz, CDCl$_3$): δ2.3 (s, 3H), 2.4 (s, 3H), 4.8 (d, 2H), 5.8 (t, 1H), 5.95 (d, 1H), 6.55 (t, 1H), 7.2 (d, 1H), 7.45–7.6 (m, 3H), 7.68 (d, 1H), 7.77 (d, 1H), 8.33 (d, 1H)

Example 1.15

Synthesis of 8-(2-ethoxycarbonyl-6-methylbenzylamino)-2,3-dimethylimidazo[1,2-a]pyridine Yield: 5%

$^1$H-NMR (300 MHz, CDCl$_3$): δ1.25 (t, 3H), 2.35 (s, 6H), 2.45 (s, 3H), 4.25 (q, 2H), 4.55 (d, 2H), 5.1 (bs, 1H), 6.2 (d, 1H), 6.7 (t, 1H), 7.2–7.35 (m, 3H), 7.65 (d, 1H)

Example 1.16

Synthesis of 8-(2-methoxy-6-methylbenzylamino)-2,3-dimethylimidazo[1,2-a]pyridine Yield: 39%

$^1$H-NMR (300 MHz, CDCl$_3$): δ2.35 (s, 6H), 2.4 (s, 3H), 3.8 (s, 3H), 4.4 (d, 2H), 4.9 (bs, 1H), 6.25 (d, 1H), 6.7–6.85 (m, 3H), 7.15 (d, 1H), 7.2 (d, 1H)

Example 1.17 was prepared according to example 1.7

Example 1.17

Synthesis of 8-(2-methoxymethyl-6-methylbenzylamino)-2,3-dimethylimidazo[1,2-a] pyridine Yield: 52%

$^1$H-NMR (500 MHz, CDCl$_3$): δ2.34 (s, 3H), 2.35 (s, 3H), 2.40 (s, 3H), 3.36 (s, 3H), 4.40 (d, 2H), 4.50 (s, 2H), 4.86 (t, 1H), 6.24 (d, 1H), 6.71–6.74 (m, 1H), 7.15–7.21 (m, 3H), 7.25 (d, 1H)

Example 1.18

Synthesis of 8-(2,6-dichlorobenzylamino)-2,3-dimethylimidazo[1,2-a]pyridine

Yield: 49%

$^1$H-NMR (300 MHz, CDCl$_3$): δ2.35 (s, 3H), 2.4 (s, 3H), 4.7 (d, 2H), 5.2 (bs, 1H), 6.3 (d, 1H), 6.7 (t, 1H), 7.1–7.4 (m, 4H)

Example 1.19

Synthesis of 8-(2,6-dibromobenzylamino)-2,3-dimethylimidazo[1,2-a]pyridine

Yield: 70%

$^1$H-NMR (500 MHz, CDCl$_3$): δ2.45 (s, 3H), 2.48 (s, 3H), 4.7 (d, 2H), 5.15 (bs, 1H), 6.3 (d, 1H), 6.7 (t, 1H), 7.0 (t, 1H), 7.25 (d, 1H), 7.55 (d, 2H)

Example 1.20

Synthesis of 2,3-dimethyl-8-(2-trifluoromethocybenzylamino)-imidazo[1,2-a] pyridine hydrochloride Yield: 51%

$^1$H-NMR (300 MHz, CDCl$_3$): δ2.3 (s, 6H), 2.4 (s, 6H), 4.55 (d, 2H), 5.7 (t, 1H), 5.95 (d, 1H), 6.5 (t, 1H), 7.1–7.3 (m, 4H), 7.45 (d, 1H)

Example 1.21

Synthesis of 2,3-dimethyl-8-(2-fluoro-6-trifluoromethylbenzylamino)-imidazo[1,2-a]pyridine hydrochloride Yield: 36%

$^1$H-NMR (300 MHz,DMSO-d6): δ2.4 (s, 3H), 2.45 (s, 3H), 4.55 (d, 2H), 6.85 (bs, 1H), 7.05 (d, 1H), 7.35 (t, 1H), 7.7 (bs, 3H), 8.0 (d, 1H)

Example 1.22

Synthesis of 2-([[(2,3-dimethylimidazo[1,2-a] pyridin-8-yl)amino]methyl)phenyl acetate methanesulfonate Yield: 58%

$^1$H-NMR (600 MHz, CDCl$_3$): δ2.04 (s, 3H), 2.43 (s, 3H), 2.57 (s, 3H), 2.68 (s, 3H), 3.08 (t, 2H), 4.31 (t, 2H), 4.60 (s, 2H), 6.47 (d, 1H), 7.03–7.06 (m 1H), 7.18–7.40 (m, 2H), 7.23–7.24 (m, 2H), 7.38–7.40 (m, 2H), 7.45 (bs, 1H), 14.64 (s, 1H)

Example 1.23

Synthesis of 8-(2-ethylbenzylamino)-2,3-dimethylimidazo[1,2-a]pyridine

Yield: 36%

$^1$H-NMR (300 MHz, CDCl$_3$): δ1.27 (t, 3H), 2.35 (s, 3H), 2.39 (s, 3H), 2.74 (q, 2H), 4.44 (d, 2H), 5.30 (t, 1H), 6.06 (d, 1H), 6.60–6.66 (m, 1H), 7.10–7.30 (m, 5H), 7.37 (d, 1H)

Example 1.24

Synthesis of 8-[1-(2,6-dimethylphenyl)ethylamino]-2,3-dimethylimidazo[1,2-a]pyridine Yield: 16%

$^1$H-NMR (300 MHz, CDCl$_3$): δ1.65 (d, 3H), 2.3 (s, 3H), 2.4 (s, 3H), 2.45 (s, 6H), 5.0 (m, 1H), 5.4 (d, 1H), 5.55 (d, 1H), 6.45 (t, 1H), 6.9–7.05 (m, 3H), 7.1 (d, 1H)

Example 1.25

Synthesis of 8-[1-(2,6-dimethylphenyl)ethoxy]-2,3-dimethylimidazo[1,2-a]pyridine Yield: 24%

$^1$H-NMR (300 MHz, CDCl$_3$): δ1.8 (d, 3H), 2.35 (s, 3H), 2.45 (s, 3H), 2.5 (s, 6H), 5.8 (q, 1H), 5.95 (d, 1H), 6.45 (d, 1H), 6.9–7.0 (m, 3H), 7.30 (d, 1H)

Example 1.26

Synthesis of 2,3-dimethyl-8-(2-[2-(methylsulfonyl)ethyl]-benzylamino)-imidazo[1,2-a]pyridine Yield: 34%

$^1$H-NMR (000 MHz, CDCl$_3$): δ2.34 (s, 6H), 2.67 (s, 3H), 3.18–3.33 (m, 4H), 4.43 (d, 2H), 5.15 (t, 1H), 6.14 (d, 1H), 6.62–6.68 (m, 1H), 7.15–7.30 (m, 4H), 7.37 (d, 1H)

Example 1.27

Synthesis of 8-(2-[2-(methylcarbonyloxy)ethyl]-4-fluoro-6-methylbenzylamino)-2,3-dimethyl-imidazo[1,2-a]pyridine Yield: 33%

$^1$H-NMR (300 MHz, CDCl$_3$): δ2.01 (s, 3H), 2.33 (s, 3H), 2.35 (s, 3H), 2.37 (s, 3H), 3.00 (t, 2H), 4.25 (t, 2H), 4.31 (d, 2H), 4.78 (bs, 1H), 6.22 (d, 1H), 6.73 (t, 1H), 6.80 (d, 2H), 7.26 (d, 1H)

Example 1.28

Synthesis of 8-(3-phenoxybenzylamino)-2,3-dimethylimidazo[1,2-a]pyridine

Yield: 20%

$^1$H-NMR (300 MHz, CDCl$_3$): δ2.3 (s, 3H), 2.4 (s, 3H), 4.4 (m, 2H), 5.5 (m, 1H), 6.0 (d,1H), 6.55(t,1H), 6.85–7.35 (m,10H)

Example 1.29

Synthesis of 8-(2,6-dimethylbenzylamino)-2,3-dimethyl-7-nitroimidazo[1,2-a]pyridine 2,3-dimethyl-8-(2,6-dimethylbenzylamino)-imidazo[1,2-a]pyridine (2.0 g, 7.16 mmol) was dissolved in acetic acid (30 ml) and nitric acid (0.53 g, 7.57 mmol) was added. The mixture was heated to 80–85° C. and stirred for 3 h at this temperature. After evaporation of the major part of the acetic acid, the residue was partitioned between methylene chloride and water. The organic layer was washed with a solution of sodium carbonate and the solvent was removed under reduced pressure. The residue was dissolved in methylene chloride (100 ml) and filtered through silica gel (10 g) whereupon the methylene chloride was removed under reduced pressure. Chromatography with methylene chloride (100%) gave 0.4 g (17%) of the title compound.

Example 1.30–1.40 were prepared according to Example 1.1

Example 1.30 and 1.31 are prepared from a mixture of 2-chloro-6-methylbenzylbromide and 3-chloro-2-methylbenzylbromide. The yields are referred to 8-amino-2,3-dimethyl-6-methylimidazo[1,2-a]pyridine.

Example 1.30

Synthesis of 8-(2-chloro-6-methylbenzylamino)-2,3,6-trimethylimidazo[1,2-a]pyridine Yield: 34%

$^1$H-NMR (300 MHz, CDCl$_3$): δ2.35 (s, 9H), 2.55 (s, 3H), 4.5 (d, 2H), 4.85 (bs, 1H), 6.1 (s, 1H), 7.05 (s, 1H), 7.1–7.3 (m, 3H)

Example 1.31

Synthesis of 8-(3-chloro-2-methylbenylamino)-2,3,6methylimidazo[1,2-a]pyridine

Yield: 27%

$^1$H-NMR (300 MHz, CDCl$_3$): δ2.25 (s, 3H), 2.35 (s, 3H), 2.4 (s, 3H), 2.45 (s, 3H), 4.4 (d, 2H), 5.25 (t, 1H), 5.85 (s, 1H), 7.0–7.1 (m, 2H), 7.25–7.35 (m, 2H)

Example 1.32 and 1.33 are prepared from a mixture of 2-bromo-6-methylbenzylbromide and 3-bromo-2-methylbenzylbromide. The yields are referred to 8-amino-2,3-dimethylimidazo[1,2-a]pyridine.

Example 1.32

Synthesis of 8-(2-bromo-6-methylbenzylamino)-2,3-dimethylimidazo[1,2-a]pyridine

Yield: 25%

$^1$H-NMR (300 MHz, CDCl$_3$): δ2.35 (s, 6H), 2.45 (s, 3H), 4.55 (d, 2H), 4.85 (bs, 1H), 6.25 (d, 1H), 6.75 (t, 1H), 7.05–7.2 (m, 2H), 7.25 (d, 1H), 7.4 (d, 1H)

Example 1.33

Synthesis of 8-(3-bromo-2-methylbenzylamino)-2,3-dimethylimidazo[1,2-a]pyridine

Yield: 16%

$^1$H-NMR (300 MHz, CDCl$_3$): δ2.35 (s, 3H), 2.4 (s, 3H), 2.45 (s, 3H), 4.45 (d, 2H), 5.35 (bs, 1H), 6.0 (d, 1H), 6.65 (t, 1H), 7.0 (t, 1H), 7.2–7.35 (m, 3H), 7.5 (d, 1H)

Example 1.34 and 1.35 are prepared from a mixture of 2-chloro-6-methylbenzylbromide and 3-chloro-2-methylbenzylbromide. The yields are referred to 8-amino-2,3-dimethylimidazo[1,2-a]pyridine.

Example 1.34

Synthesis of 8-(2-chloro-6-methylbenzylamino)-2,3-dimethylimidazo[1,2-a]pyridine Yield: 24%

$^1$H-NMR (300 MHz, CDCl$_3$): δ2.35 (s, 6H), 2.45 (s, 3H), 4.5 (d, 2H), 4.85 (bs, 1H), 6.25 (d, 1H), 6.7 (t, 1H), 7.1–7.35 (m, 4H)

Example 1.35

Synthesis of 8-(3-chloro-2-methylbenzylamino)-2,3-dim ethylimidazo[1,2-a]pyridine Yield: 19%

$^1$H-NMR (300 MHz, CDCl$_3$): δ2.35 (s, 3H), 2.4 (s, 3H), 2.45 (s, 3H), 4.45 (d, 2H), 5.3 (t, 1H), 6.0 (d, 1H), 6.6 (t, 1H), 7.05 (t, 1H), 7.25–7.35 (m, 3H)

Example 1.36

Synthesis of 8-(2-chloro-4,6-dimethylbenzylamino)-2,3-dimethylimidazo[1,2-a]pyridine Yield: 7%

$^1$H-NMR (300 MHz, CDCl$_3$): δ2.28 (s, 3H), 2.34 (s, 6H), 2.38 (s, 3H), 4.46 (d, 2H), 4.86 (t, 1H), 6.22 (d, 1H), 6.28–6.74 (m, 1H), 6.90 (s, 1H), 7.07 (s, 1H), 7.25 (d, 1H)

Example 1.37

Synthesis of 8-(2,4-dichloro-6-methylbenzylamino)-2,3-dimethylimidazo[1,2-a]pyridine Yield: 28%

$^1$H-NMR (500 MHz, CDCl$_3$): δ2.34 (s, 3H), 2.35 (s, 3H), 2.41 (s, 3H), 4.46 (d, 2H), 4.86 t, 1H), 6.21 (d, 1H) 6.69–6.72 (m, 1H), 7.10 (d, 1H), 7.24–7.28 (m,2H)

Example 1.38

Synthesis of 8-(2-cyano-6-methylbenzylamino)-2,3-dimethylimidazo[1,2-a]pyridine

Yield: 49%

$^1$H-NMR (300 MHz, CDCl$_3$): δ2.35 (s, 6H), 2.45 (s, 3H), 4.6 (d, 2H), 4.95 (bs, 1H), 6.25 (d, 1H), 6.7 (t, 1H), 7.25–7.35 (m, 2H), 7.4 (d, 1H), 7.55 (d, 1H)

Example 1.39

Synthesis of 8-(3-cyano-2-methylbenzylamino)-2,3-dimethylimidazo[1,2-a]pyridine

Yield: 26%

$^1$H-NMR (300 MHz, CDCl$_3$): δ2.35 (s, 3H), 2.4 (s, 3H), 2.6 (s, 3H), 4.45 (d, 2H), 5.35 (t, 1H), 5.95 (d, 1H), 6.65 (t, 1H), 7.2–7.3 (m, 2H), 7.55 (t, 2H)

Example 1.40

Synthesis of 8-(3-difluoromethoxybenzylamino)-2,3-dimethylimidazo[1,2-a]pyridine hydrochloride Yield: 45%

$^1$H-NMR (300 MHz, CDCl$_3$): δ2.25 (s, 3H), 2.35 (s, 3H), 4.5 (d, 2H), 5.65 (t, 1H), 5.95 (d, 1H), 6.5 (d, 1H), 6.55 (t, 1H), 7.0–7.25 (m, 4H), 7.4 (d, 1H)

Example 7 41–45 were prepared according to Example 7.

Example 1.41

Synthesis of 8-(2-methoxymethyl-6-methylbenzylamino)-2,3,6-trimethylimidazo[1,2-a]pyridine Yield: 60%

$^1$H-NMR (300 MHz, CDCl$_3$): δ2.25 (s, 3H), 2.3 (s, 6H), 2.4 (s, 3H), 3.35 (s, 3H), 4.4 (d, 1H), 4.5 (s, 3H), 4.85 (bs, 1H), 6.1 (s, 1H), (7.0 s, 1H), 7.05–7.2 (m, 3H)

Example 1.42

Synthesis of8-(2,6-dimethyl-3-nitrobenzylamino)-2,3-dimethylimidazo[1,2-a]pyridine Yield: 15%

$^1$H-NMR (300 MHz, CDCl$_3$): δ2.32 (s, 3H), 2.35 (s, 3H), 2.45 (s, 3H), 2.5 (s, 3H), 4.4 (d, 2H), 4.75 (m, 1H), 6.22 (d, 1H), 6.75 (t, 1H), 7.17 (d, 1H), 7.3 (d,1H), 7.7 (d,1H)

Example 1.43

Synthesis of 2,3-dimethyl-8-[2-(2-methoxyethyl)-6-methylbenylamino]-6-methylimidazo[1,2-a]pyridine hydrochloride Yield: 11%

$^1$H-NMR (300 MHz, CDCl$_3$): δ2.35 (s, 3H), 2.38 (s, 3H), 2.44 (s, 3H), 2.46(s, 3H), 3.02 (t, 2H), 3.30 (s, 3H), 3.59 (t, 2H), 4.41 (s, 2H), 6.46 (s, 1H), 7.10–7.35 (m, 4H)

Example 1.44

Synthesis of 8-[2,6-dimethylbenzylamino]-2,3,7-trimethylimidazo[1,2-a]pyridine hydrochloride Yield: 11%

$^1$H-NMR (300 MHz, CDCl$_3$): δ2.35 (s, 9H), 2.4 (s, 3H), 2.6 (s, 3H), 4.65 (s, 2H), 6.95–7.15 (m, 4H), 7.5 (bs, 1H), (neutral form)

Example 1.45

Synthesis of 2,3-dimethyl-8-[(2,4-dimethyl-3-thienyl)methylamino]-imidazo[1,2-a]pyridine Yield: 44%

$^1$H-NMR (300 MHz, CDCl$_3$): δ2.2 (s, 3H), 2.35 (s, 3H), 2.36 (s, 3H), 2.45 (s, 3H), 4.2 (d, 2H), 4.8 (bs, 1H), 6.2 (d, 1H), 6.65–6.75 (d, 2H), 7.25 (d, 1H)

Example 1.46

Synthesis of 2,6-dimethyl-3-hydroxymethyl-8-(2-methoxymethyl-6-methylbenzylamino)-imidazo[1,2-a]pyridine lithium aluminum hydride (0.29 g, 7.7 mmol) was added to tetrahydrofuran (30 ml) and 3-carbethoxy-8-(2-methoxymethyl-6-methylbenzylamino)-2-methylimidazo[1,2-a]pyridine (1.4 g, 3.8 mmol) dissolved in tetrahydrofuran (30 ml) was added dropwise during 80 min. at room temperature and stirred for 4 h. Water (0.29 ml) was added dropwise, followed by sodium hydroxide (15%, 0.29 ml) and finally 0.93 ml of water. After stirring 30 min. the solids were filtered off and washed thoroughly with tetrahydrofuran. The solvent was removed under reduced pressure and chromatography on silica gel (methylene chloride:methanol, 9:1) gave (0.97 g 75%) of the title compound as a white solid.

$^1$H-NMR (300 MHz, CDCl$_3$): δ2.0 (s, 3H), 2.3 (s, 3H), 2.4 (s, 3H), 3.35 (s, 3H), 3.6 (bs,1H) 4.4 (d, 2H), 4.5 (s, 2H), 4.6 (s, 2H), 4.9 (bs, 1H), 6.15 (s, 3H), 7.1–7.25 (m, 3H), 7.35 (s, 1H)

Example 1.47 was prepared according to Example 1.46

Example 1.47

Synthesis of 8-(2-chloro-6-methylbenzylamino)-2,6-dimethyl-3-hydroxymethylimidazo[1,2-a]pyridine Yield: 46%

$^1$H-NMR (300 MHz, CDCl$_3$): δ2.25 (s, 3H), 2.3 (s, 3H), 2.45 (s, 3H), 4.5 (d, 2H), 4.8 (s, 2H), 4.85 (bs, 1H), 6.2 (s, 1H), 7.1–7.25 (m, 3H), 7.4 (s, 1H)

Example 1.48–1.49 were prepared according to Example 1.1

Example 1.48

Synthesis of 8-(2,6-dimethylbenzylamino)-2-methylimidazo[1,2-a]pyridine

Yield: 70%

$^1$H-NMR (300 MHz, CDCl$_3$): δ2.35 (s, 9H), 4.3 (d, 2H), 4.8 (bs, 1H), 6.2 (d, 1H), 6.65 (t, 1H), 7.0–7.15 (m, 3H), 7.25 (s, 1H), 7.45 (d, 1H)

Example 1.49

Synthesis of 8-(4-fluoro-2,6-dimethylbenzylamino)-2-methylimidazo[1,2-a]pyridine Yield: 71%

$^1$H-NMR (300 MHz, CDCl$_3$): δ2.35 (s, 6H), 2.4 (s, 3H), 4.3 (d, 2H), 4.75 (bs, 1H), 6.2 (d, 1H), 6.65 (t, 1H), 6.75 (d, 2H), 7.25 (s, 1H), 7.5 (d, 1H)

Example 1.51

Synthesis of 2,6-dimethyl-8-(4-fluoro-2,6-dimethylbenzylamino)-imidazo[1,2-a]pyridine A mixture of 8-(4-fluoro-2,6-dimethylbenzylamino)-2-methyl-6-methylimidazo[1,2-a]pyridine 3-carboxylic acid (0.35 g, 1.03 mmol) and diphenyl ether and refluxed for 10 min. Petroleum ether 40–60 was added at room temperature followed by hydrogen chloride in diethyl ether. The petroleum ether diphenlether layer was removed from the formed precipitate. The precipitate was washed with petroleum ether thereafter dissolved in methylene chloride and basified with sodium hydroxide (2M). The layers were separated and the organic layer was washed with water. The solvent was evaporated and the residue was chromatographed (hexane:ethyl acetate, 2:1) giving 0.17 g (50%) of the title compound.

$^1$H-NMR (300 MHz, CDCl$_3$): δ2.25 (s, 1H), 2.35 (s, 9H), 4.25 (d, 2H), 4.75 (bs, 1H), 6.05 (s, 1H), 6.75 (d, 2H), 7.1 (s, 1H), 7.25 (s, 1H)

Example 1.52 were prepared according to example 1.51

Example 1.52

Synthesis of 2,6-dimethyl-8-(2,6-dimethylbenzylamino)-imidazo[1,2-a]pyridine

Yield: 40% $^1$H-NMR (300 MHz, CDCl$_3$): δ2.25 (s, 1H), 2.35 (s, 3H), 2.4 (s, 6H), 4.3 (d, 2H), 4.75 (bs, 1H), 6.05 (s, 1H), 6.95–7.15, (m, 4H), 7.2 (s, 1H)

Example 1.53

Synthesis of 8-(2,6-dimethylbenzylamino)-3-ethyl-2-methylimidazo[1,2-a]pyridine hydrochloride To a stirred mixture of 1-[8-(2,3-dimethylbenzylamino)-2-methylimidazo[1,2-a]pyridine-3-yl]-1-ethanol (0.3 g, 0.98 mmol), boron trifluoride diethyl etherate (0.14 ml, 3.2 mmol) in tetrahydrofuran (10 ml) was added sodium cyanoborohydride (0.13 g, 2.0 mmol). The reaction mixture was stirred for 2.5 h and the solvent was evaporated under reduced pressure. The residue was solved in methylene chloride and was washed twice with a saturated sodium bicarbonate solution. The organic layer was separated, dried and evaporated under reduced pressure. Purification twice by column chromatography on silica gel using 1) methylene chloride: ethyl acetate (100:7) 2) methylene chloride:methanol (100:3) as eluent and treating with HCl/diethyl ether gave 0.1 g (31%) of the title compound.

$^1$H-NMR (300 MHz, CDCl$_3$): δ1.2 (t, 1H), 2.35 (s, 3H), 2.4 (s, 6H), 2.85 (q, 2H), 4.35 (d, 2H), 4.8 (bs, 1H), 6.2 (d, 1H), 6.7 (t, 1H), 7.05–7.15 (m, 3H), 7.35 (d, 1H)

Example 1.54

Synthesis of 8-(2,6-dimethylbenzylamino)-2-methyl-3-vinylimidazo[1,2-a]pyridine

A mixture of 1-[8-(2,3-dimethylbenzylamino)-2-methylimidazo[1,2-a]pyridine-3-yl]-1-ethanol (0.2 g, 0.65 mmol) and p-toluenesulfonic acid (0.029 g, 0.15 mmol) in benzene (40 ml) was refluxed for 20 h with Dean-Stark water separation. The solvent was evaporated under reduced pressure, the residue was solved in methylene chloride and washed with saturated sodium bicarbonate solution. The organic layer was separated, dried and evaporated under reduced pressure. Purification of the residue by column chromatography on silica gel using methylene chloride: ethyl acetate (10:1) gave 0.062 g (33%) of the title compound.

$^1$H-NMR (300 MHz, CDCl$_3$): δ2.4 (s, 6H), 2.5 (s, 3H), 4.35 (d, 2H), 4.85 (bs, 1H), 5.35 (d, 1H), 5.55 (d, 1H), 6.25 (d, 1H), 6.75–6.85 (m, 2H), 7.05–7.15 (m, 3H), 7.6 (d, 1H)

Example 1.55

Synthesis of 2-cyanomethyl-8-(2,6-dimethylbenzylamino)-3-methylimidazo[1,2-a]pyridine 2-chloromethyl-8-(2,6-dimethylbenzylamino)-3-methylimidazo[1,2-a]pyridine (2.4 mmol) and potassium cyanide (2.4 mmol) were added to dimethyl sulfoxide (25 ml) and stirred for 2 h. at room temperature. Methylene chloride and water were added to the reaction mixture and the organic layer was separated, dried (Na$_2$SO$_4$) and evaporated under reduced pressure. The residue was purified by by column chromatography on silica gel using methylene chloride:methanol (10:1) as eluent. Crystallization from acetonitrile gave 0.25 g (34%) of the title compound.

$^1$H-NMR (500 MHz, CDCl$_3$): δ2.4 (s, 6H), 2.45 (s, 3H), 3.8 (s, 2H), 4.35 (d, 2H), 4.8 (bs, 1H), 6.3 (d, 1H), 6.8 (t, 1H), 7.1 (d, 2H), 7.15 (t, 1H), 7.3 (t, 1H)

Example 1.56

Synthesis of 8-(2,6-dimethylbenzylamino)-3-methyl-2-methylsulfanylmethyl-imidazo[1,2-a]pyridine 2-chloromethyl-8-(2,6-dimethylbenzylamino)-3-methylimidazo[1,2-a]pyridine (0.2 g, 0.64 mmol) and sodium methanethiolate (0.1 g, 1.3 mmol) were added to acetonitrile(10 ml) and stirred for 4 h. at room temperature. The solvent was evaporated under reduced pressure and to the residue were added methylene chloride and water. The organic layer was separated, dried (Na$_2$SO$_4$) and evaporated under reduced pressure. Purification of the residue by column chromatography on silica gel using diethyl ether:petroleum ether (1:2) as eluent and crystallization from diethyl ether:petroleum ether (1:2) gave 0.05 g (24%) of the desired product.

$^1$H-NMR (400 MHz, CDCl$_3$): δ2.1 (s, 3H), 2.4 (s, 6H), 2.45 (s, 3H), 3.85 (s, 2H), 4.4 (s, 2H), 4.9 (bs, 1H), 6.25 (d, 1H), 6.75 (t, 1H), 7.1 (d, 2H), 7.15 (t, 1H), 7.3 (d, 1H)

Example 1.57

Synthesis of 8-(2,6-dimethylbenzylamino)-2-methoxymethyl-3-methyl-imidazo[1,2-a]pyridine 2-chloromethyl-8-(2,6-dimethylbenzylamino)-3-methylimidazo[1,2-a]pyridine (0.3 g, 0.96 mmol) was solved in methanol (20 ml) and stirred for 20 h. at room temperature and refluxed for 20 min. The solvent was evaporated under reduced pressure and the residue was dissolved in methylene chloride and washed with a bicarbonate solution. The organic layer was separated, dried ($Na_2SO_4$) and evaporated under reduced pressure. Purification of the residue by column chromatography on silica gel using diethyl ether:petroleum ether (2:1) as eluent and crystallization from diethyl ether:petroleum ether (2:1) gave 0.13 g (44%) of the desired product.

$^1$H-NMR (500 MHz, $CDCl_3$): δ2.4 (s, 6H), 2.45 (s, 3H), 3.4 (s, 3H), 4.35 (d, 2H), 4.55 (s, 2H), 4.95 (bs, 1H), 6.25 (d, 1H), 6.8 (t, 1H), 7.05 (d, 2H), 7.15 (t, 1H), 7.3 (d, 1H)

Example 1.58

Synthesis of 2-aminocarbonylmethyl-3-methyl-8-(2,6-dimethylbenzylamino)-7-imidazo[1,2-a]pyridine A mixture of Example 55 (40 mg, 0.13 mmol), potassium hydroxide (30 mg) in t-butanol 1.0 ml was refluxed for 10 minutes. The mixture was filtered and methylene chloride (2 ml) was added to the filtrate and washed with water. The organic layer was dried over sodium sulfate and evaporated giving 26 mg (64%) of the title compound.

$^1$H-NMR (300 MHz, $CDCl_3$): δ2.35 (s, 3H), 2.4 (s, 6H), 3.6 (s, 2H), 4.35 (d, 2H), 4.8 (bs, 1H), 5.55 (bs, 1H), 6.3 (d, 1H), 6.8 (t, 1H), 7.0–7.35 (m, 5H)

Example 1.59

Synthesis of 8-(2-hydroxymethyl-6-methylbenzylamino)-2,3-dimethylimidazo[1,2-a]pyridine hydrochloride To an icecooled mixture of 2-(((2,3-dimethylimidazo[1,2-a]pyridin-8-yl)amino)methyl)-3-methylbenzoic acid (0.18 g, 0.59,mmol) in toluene (30 ml) was added dropwise Red-Al (5 ml) in toluene (7 ml) and was stirred at room temperature for 20 h. The mixture was cooled with ice and water (10 ml) and methylene chloride were added. After filtration the filtrate was evaporated under reduced pressure and the residue was purified by column chromatography on silica gel using methylene chloride:methanol (100:5) as eluent. The product was solved in methylene chloride/ether and treated with HCl/diethyl ether to give 0.024 g (12%) of the title compound.

$^1$H-NMR (300 MHz, $CDCl_3$): δ2.25 (s, 3H), 2.3 (s, 3H), 2.4 (s, 3H), 4.4 (d, 1H), 4.65 (s, 2H), 5.05 (bs, 1H), 6.25 (d, 1H), 6.75 (t, 1H), 7.1–7.25 (m, 4H)

Example 1.60

Synthesis of 8-(2-hydroxy-6-methylbenzylamino)-2,3-dimethylimidazo[1,2-a]pyridine 8-(2-methoxy-6-methylbenzylamino)-2,3-dimethylimidazo[1,2-a]pyridine (0.14 g, 0.48 mmol) was solved in methylene chloride (9 ml) and the mixture was cooled to −73° C. Boron tribromide in methylene chloride (1M) (2.37 ml, 2.37 mmol) was added dropwise and the mixture was stirred for 20 h. in a nitrogen atmosphere and the temperature was allowed to raise to room temperature. The reaction mixture was cooled on ice and ice, water and methylene chloride were added. The organic layer was separated, washed with saturated sodium bicarbonate, dried and evaporated under reduced pressure to give 0.077 g (57%) of the title compound.

$^1$H-NMR (500 MHz, $CDCl_3$): δ2.25 (s, 3H), 2.35 (s, 3H), 2.4 (s, 3H), 4.4 (d, 2H), 4.95 (t, 1H), 6.3 (d, 1H), 6.55 (d, 1H), 6.7 (t, 1H), 6.8 (d, 1H), 6.9 (t, 1H) 7.25 (d, 1H)

Example 1.61

Synthesis of 8-(2-aminomethyl-6-methylbenzylamino)-2,3-dimethylimidazo[1,2-a]pyridine To a solution of 8-(2-cyano-6-methylbenzylamino)-2,3-dimethylimidazo[1,2-a]pyridine (0.42 g, 1.44 mmol) in ammonia saturated ethanol/methanol (10/2.5)(30 ml) was added Raney nickel (50% in water)(0.45 g) The mixture was hydrogenated at room temperature and atmospheric pressure until the uptake of hydrogen ceased. Following filtration through celite, the solvents were evaporated under reduced pressure and the residue was purified by by column chromatography on silica gel using methylene chloride:methanol (10:2) as eluent. Recrystallization from methylene chloride/diethyl ether gave 0.052 g (12%) of the desired product.

$^1$H-NMR (300 MHz, $CDCl_3$): δ2.35 (s, 6H), 2.4 (s, 3H), 3.95 (s, 2H), 4.4 (s, 2H), 6.25 (d, 1H), 6.75 (t, 1H), 7.1–7.25 (m, 4H)

Example 1.62

Synthesis of methyl N-(2-(((2,3-dimethylimidazo[1,2-a]pyridine-8-yl)amino)methyl)-3-methylbenzyl) carbamate To an ice cooled solution of 8-(2-aminomethyl-6-methylbenzylamino)-2,3-dimethylimidazo[1,2-a]pyridine (0.17 g, 0.58 mmol), pyridine (0.046 g, 0.58 mmol) in methylene chloride (8 ml) was added methyl chloroformate (0.055 g, 0.58 mmol) and the reaction mixture was stirred for 1.5 h. and the temperature was allowed to raise to 12° C. Methylene chloride was added and the solution was washed twice with water. The organic layer was separated, washed with saturated sodium bicarbonate, dried and evaporated under reduced pressure. The residue was purified by by column chromatography on silica gel using methylene chloride:methanol (100:5) as eluent. Recrystallization from diethyl ether gave 0.052 g (25%) of the title compound.

$^1$H-NMR (300 MHz, $CDCl_3$): δ2.35 (s, 6H), 2.45 (s, 3H), 3.55 (s, 3H), 4.4 (d, 2H), 4.45 (d, 2H), 4.75 (bs, 1H), 5.25 (bs, 1H), 6.25 (d, 1H), 6.75 (t, 1H), 7.1–7.3 (m, 4H

Example 1.63

Synthesis of 2-(((2,3-dimethylimidazo[1,2-a]pyridine-8-yl)amino)methyl)-3-methylphenyl methyl carbonate hydrochloride A mixture of 8-(2-hydroxy-6-methylbenzylamino)-2,3-dimethylimidazo[1,2-a]pyridine (0.068 g, 0.24 mmol) sodium carbonate (0.12 g, 1.1 mmol), and potassium hydroxide (0.019 g, 0.34 mmol) in acetone (12 ml) was stirred for 15 min in room temperature in a nitrogen atmosphere. Methyl chloroformate (0.023 g, 0.24 mmol) was added and the reaction mixture was stirred for 70 min. Methylene chloride was added and the mixture was filtered and the filtrate was evaporated under reduced pressure. The residue was dissolved in methylene chloride, washed with saturated sodium bicarbonate and water and the organic layer was separated, dried and evaporated under reduced pressure. The residue was purified by by column chromatography on silica gel using methylene chloride:methanol (100:5) as eluent and treated with HCl/diethyl ether to give 0.025 g (28%) of the title compound.

$^1$H-NMR (300 MHz, CDCl$_3$): δ2.35 (s, 3H), 2.5 (s, 3H), 2.6 (s, 3H), 3.9 (s, 3H), 4.5 (d, 2H), 6.75 (d, 1H), 6.95–7.3 (m, 5H), 8.0 (t, 1H), 15.6 (bs, 1H)

Example 1.64

Synthesis of 2-(2-(((2,3-dimethylimidazo[1,2-a]pyridin-8-yl)amino)methyl)-3-methylphenoxy)-1-ethanol To a solution of 8-(2-hydroxy-6-methylbenzylamino)-2,3-dimethylimidazo[1,2-a]pyridine (0.14 g, 0.5 mmol) in N,N-dimethylformamide (3 ml) was added lithium hydride (0.004 g, 0.51 mmol) and the mixture was stirred for 10 min at 100° C. Ethylene carbonate (0.055 g, 0.63 mmol) was added and the mixture was stirred for 10 min at 130° C. Tetramethylammonium iodide (0.054 g, 0.63 mmol) was added and the mixture was stirred for 12 h. at 140–145° C. The solvent was evaporated under reduced pressure and the residue was solved in methylene chloride, washed twice with saturated sodium bicarbonate. The organic layer was separated, dried and evaporated under reduced pressure and the residue was purified by column chromatography on silica gel using methylene chloride:methanol (100:6) as eluent to give 0.067 g (41%) of the title compound.

$^1$H-NMR (500 MHz, CDCl$_3$): δ2.3 (s, 3H), 2.35 (s, 3H), 2.45 (s, 3H), 4.0 (t, 2H), 4.15 (t, 2H), 4.5 (d, 2H), 6.25 (d, 1H), 6.35 (t, 1H), 6.7 (t, 1H), 6.75 (d, 1H), 6.8 (d, 1H), 7.1 (t, 1H), 7.2 (d, 1H)

Example 1.65

Synthesis of 2-(((2,3-dimethylimidazo[1,2-a]pyridin-8-yl)amino)methyl)-3-methylphenyl trifluoromethanesulfonate To a solution of 8-(2-hydroxy-6-methylbenzylamino)-2,3-dimethylimidazo[1,2-a]pyridine (0.1 g, 0.32 mmol) in methylene chloride (7 ml) was added triethyl amine (0.07 g, 0.69 mmol) and the reaction mixture was cooled on ice. N,N-dimethylamino pyridine (0.077 g, 10 mmol) and trifluoromethanesulfonic anhydride (0.12 g, 0.41 mmol) in methylene chloride (0.5 ml) and N-phenyltrifluoromethanesulfonimide (0.28 g, 0.78 mmol) and potassium carbonate (0.38 g, 2.7 mmol) were added and the reaction mixture was stirred for 135 min. at 18° C. Methylene chloride was added and the solution was washed with water/NH$_4$Cl, saturated sodium bicarbonate and water. The organic layer was separated, dried, and evaporated under reduced pressure. Purification of the residue by column chromatography on silica gel using methylene chloride:ethyl acetate (10:2) as eluent and crystallization from diethyl ether/petroleum ether gave 0.053 g (40%) of the title compound.

$^1$H-NMR (500 MHz, CDCl$_3$): δ2.33 (s, 3H), 3.35 (s, 3H), 2.45 (s, 3H), 4.45 (d, 2H), 5.0 (bs, 1H), 6.25 (d, 1H), 6.75 (t, 1H), 7.15 (d, 1H), 7.2–7.35 (m, 3H)

Example 1.66

Synthesis of 8-[2-(2-hydroxyethyl)benzylamino]-2,3-dimethylimidazo[1,2-a]pyridine A mixture of Example 22 (xCH3SO3H) (0.8 g, 1.85 mmol) and sodium hydroxide (0.2 g) were refluxed in ethyl alcohol for 3 hours. The solvent was evaporated and methylene chloride/water were added to the residue. The organic layer was dried over sodium sulfate and the solvent removed under reduced pressure. Trituration of the solid residue with diethyl ether gave 0.48 g ( 88%) of the title compound.

$^1$H-NMR (300 MHz, CDCl$_3$): δ2.33 (s, 3H), 2.34 (s, 3H), 2.91 (t, 2H), 3.50 (bs, 1H), 3.87 (t, 2H), 4.40 (s, 2H), 5.63 (bs, 1H), 6.12 (d, 1H), 6.62–6.68 (m, 1H), 7.14–7.27 (m, 4H), 7.36 (d, 1H)

Example 1.67

Synthesis of 2,3-dimethyl-8-(2,6-dimethylbenzylamino)-6-hydroxymethyl-imidazo[1,2-a]pyridine To a stirred solution of ethyl 2,3-dimethyl-8-(2,6-dimethylbenzylamino)-imidazo[1,2-a]pyridine-6-carboxylate (1.2 g, 3.4 mmol) in tetrahydrofuran (30 ml) was added LiALH$_4$ (0.7 g, 18.5 mmol) during 20 min. at 5° C. 0.7 ml of water was added dropwise, followed by 0.7 ml of 15% sodium hydroxide and then 2.1 ml of water. The solids were removed by filtration and washed thoroughly with methylene chloride: methanol (1:1). The filtrate and washings were combined and the solvents were removed under reduced pressure. The residue was purified by column chromatography on silica gel using methylene chloride:methanol (10:1) as eluent. Treating the residue with diethyl ether and filtration gave 0.7 g (67%) of the title compound.

$^1$H-NMR (400 MHz, CDCl$_3$): δ2.35 (s, 6H), 2.4 (s, 6H), 4.35 (d, 2H), 4.65 (s, 2H), 4.9 (bs, 1H), 6.2 (s, 1H), 7.05–7.15 (m, 3H), 7.25 (s, 1H)

Example 1.68

Synthesis of 2,3-dimethyl-8-(2,6-dimethylbenzylamino)-6-methoxymethyl-imidazo[1,2-a]pyridine hydrochloride To a stirred solution of 2,3-dimethyl-8-(2,6-dimethylbenzylamino)-6-hydroxymethyl-imidazo[1,2-a]pyridine (0.08 g, 0.26 mmol) in methylene chloride (5 ml) was added thionyl chloride (0.038 ml, 0.52 mmol) and the mixture was stirred for 2 h. A saturated bicarbonate solution was added and the organic layer was separated, dried (Na$_2$SO$_4$) and evaporated under reduced pressure. To the residue was added methanol (5 ml) the mixture was stirred overnight. The solvent was evaporated under reduced pressure and the residue was purified by column chromatography on silica gel using methylene chloride: methanol (100:5) as eluent. Treating the residue with HCl/diethyl ether and filtration gave 0.01 g (11%) of the title compound.

$^1$H-NMR (300 MHz, CDCl$_3$): δ2.35 (s, 3H), 2.4 (s, 3H), 2.45 (s, 6H), 3.55 (s, 3H), 4.35 (d, 2H), 4.45 (s, 2H), 4.85 (bs, 1H), 6.2 (s, 1H), 7.05–7.15 (m, 3H), 7.3 (s, 1H)

Example 1.69

Synthesis of N-(8-((2,6-dimethylbenzyl)amino)-2,3-dimethylimidazo[1,2-a]pyridin-7-yl)acetamide 7-amino-2,3-dimethyl-8-(2,6-dimethylbenzylamino)-imidazo[1,2-a]pyridine (example 77) (0.16 g, 0.53 mmol) was dissolved in methylene chloride (5 ml) and acetic anhydride (60 mg) was added. The mixture was stirred over night at ambient temperature. A small amount of triethylamine was added and the solvent was removed under reduced pressure. Chromatography first with methylene chloride:methanol, 95:5 and secondly with methylene chloride:ethyl acetate, 50:50 gave after trituration with diethyl ether 87 mg (47%) as white solid.

$^1$H-NMR (300 MHz, CDCl$_3$): δ2.00 (s, 3H), 2.35 (s, 6H), 2.39 (s, 6H), 4.0 (bs 1H), 4.36 (d, 2H), 7.0–7.15 (m, 3H), 7.44 (d, 1H). 7.55 (d, 1H), 7.65 (bs, 1H)

Example 1.70

Synthesis of N-(8-((2,6-dimethylbenzyl)amino)-2,3-dimethylimidazo[1,2-a]pyridin-7-yl)-N-methylsulfonylmethanesulfonamide 7-amino-2,3-dimethyl-8-(2,6-dimethylbenzylamino)-imidazo[1,2-a]pyridine (example 77) (0.1 g, 0.34 mmol) was dissolved in methylene chloride (2 ml) followed by sodium carbonate (0.2 g, 1.9 mmol) and methanesulfonyl chloride (0.1 g, 0.87 mmol). The mixture was stirred at ambient temperature for 30 min. and after addition of 2 ml of water the mixture was stirred for 1 h. The organic layer was dried over sodium sulfate and the solvent evaporated in vacuo. Chromatography of the residue with methylene chloride-:ethyl acetate 50:50, gave 4 mg (2.6%) of the desired compound.

$^1$H-NMR (300 MHz, CDCl$_3$): δ2.35 (s, 3H), 2.36 (s, 3H), 2.40 (s, 6H), 3.34 (s, 6H), 4.7 (t, 1H), 5.09 (d, 2H), 6.54 (d, 1H), 7.05–7.15 (m, 3H), 7.24 (d, 1H)

Example 1.71

Synthesis of N-(8-((2,6-dimethylbenyl)amino)-2,3-dimethylimidazo[1,2-a]pyridin-7-yl)(trifluoro)methanesulfonamide A mixture of 7-amino-2,3-dimethyl-8-(2,6-dimethylbenzylamino)-imidazo[1,2-a]pyridine (example 77) (0.1 g, 0.34 mmol), N-phenyl-bis(trifluoromethanesulfon)-amide (125 mg,0.35 mmol) and 3 ml of acetonitrile was refluxed for 20 h. The solvent was evaporated in vacuo and the residue was chromatographed with methylene chloride:methanol, 97:3 as the eluent. The isolated product was treated with ethyl acetate and diethyl ether and 23 mg (16%) was obtained.

$^1$H-NMR (300 MHz, CDCl$_3$): δ2.16 (s, 6H), 2.22 (s, 3H), 2.23 (s, 3H), 3.85 (bs, 2H), 4.12 (s, 2H), 6.70 (d, 1H), 6.85–7.0 (m, 3H), 7.56 (d, 1H)

Example 1.72

Synthesis of 8-(2,6-dimethyl-4-fluorobenyloxy)-3-chloro-2-methylimidazo[1,2-a]pyridine To a solution of 8-(2,6-dimethyl-4-fluorobenzyloxy)-2-methylimidazo[1,2-a]pyridine (0.6 g, 2.1 mmol) in acetic acid (13 ml) was added dropwise 1.1 M Cl$_2$ in acetic acid (2.2 ml, 2.43 mmol). The reaction mixture was stirred for 2 h. at room temperature and the solvent was evaporated under reduced pressure. The residue weas solved in methylene chloride and was washed with water. The organic layer was separated, dried and evaporated under reduced pressure. The residue was purified by column chromatography on silica gel using methylene chloride:ethyl acetate (100:4) as eluent. Treating the residue with diethyl ether and filtration gave 0.3 g (45%) of the title compound.

$^1$H-NMR (300 MHz, CDCl$_3$): δ2.4 (s, 6H), 2.45 (s, 3H), 5.2 (s, 2H), 6.65 (d, 1H), 6.75 (d, 2H), 6.8 (t, 1H), 7.7 (d, 1H)

Example 1.73

Synthesis of 8-(2-(2,6-dimethylphenyl)ethenyl)-2,3-dimethylimidazo[1,2-a]pyridine To an icecooled suspension of sodium hydride (0.2 g, 5 mmol) (50% in oil) in 1,2-dimethoxyethane (2 ml) was added diethyl (2,3-dimethylimidazo[1,2-a]pyridin-8-yl) methyl phosphonate and 2,6-dimethylbenzaldehyd. The reaction mixture was stirred in a nitrogen atmosphere for 1 h. at 0° C. and for 80 min at room temperature. The solvent was decanted and evaporated under reduced pressure. The residue was solved in methylene chloride and was washed with saturated sodium bicarbonate. The organic layer was separated, dried and evaporated under reduced pressure. Purification of the residue by column chromatography on silica gel using petroleum ether:ethyl acetate (30:8) as eluent gave 0.4 g (69%) of the title compound.

$^1$H-NMR (300 MHz, CDCl$_3$): δ2.45 (s, 9H), 2.5 (s, 3H), 6.85 (t, 1H), 7.05 (s, 3H), 7.1 (d, 1H), 7.25 (d, 1H), 7.75 (d, 1H), 7.95 (d, 1H)

Example 1.74

Synthesis of 8-(2,6-dimethylphenetyl)-2,3-dimethylimidazo[1,2-a]pyridine 8-(2-(2,6-dimethylphenyl)ethenyl)-2,3-dimethylimidazo[1,2-a]pyridine was solved in methanol (3 ml) and ethanol (2 ml) and Pd/C (10%) (40 mg) was added. The mixture was hydrogenated at room temperature and atmospheric pressure until the uptake of hydrogen ceased. Following filtration through celite, the solvents were evaporated under reduced pressure to give the title compound, (0.069 g, 100%).

$^1$H-NMR (300 MHz, CDCl$_3$): δ2.35 (s, 6H), 2.4 (s, 3H), 2.45 (s, 3H), 3.05–3.2 (m, 4H), 6.7 (t, 1H), 6.85 (d, 1H), 7.0 (s, 3H), 7.7 (d, 1H)

Example 1.75

Synthesis of N-((2,3-dimethylimidazo[1,2-a]pyridin-8-yl)methyl)-2,6-dimethylaniline hydrochloride 8-chloromethyl-2,3-dimethylimidazo[1,2-a]pyridine (0.06 g, 0.31 mmol), 2,6-dimethylaniline (0.039 g, 0.32 mmol), sodium carbonate (0.15 g, 1.4 mmol) and sodium iodide (0.06 g, 0.4 mmol) in acetone (3 ml) was stirred for 20 h. at room temperature. Methylene chloride was added and the solids were isolated by filtration and the solvents were evaporated under reduced pressure. The residue was purified by column chromatography on silica gel using methylene chloride:methanol (2:1). The oily product was solved in methylene chloride and treated with HCl/diethyl ether to give the title compound, 0.02 g. (18%).

$^1$H-NMR (300 MHz, CDCl$_3$): δ2.25 (s, 6H), 2.4 (s, 3H), 2.45 (s, 3H), 4.5 (s, 2H), 6.7 (t, 1H), 6.8 (t, 1H), 6.95 (d, 2H), 7.05 (d, 1H), 7.75 (d, 1H) (base)

Example 1.76

Synthesis of 8-((2,6-dimethylphenoxy)methyl)-2,3-dimethylimidazo[1,2-a]pyridine

To a suspension of potassium hydroxide (0.035 g, 0.62 mmol), 2,6-dimethylphenol (0.075 g, 0.62 mmol) and 18-crown-6 (0.035 g) in 1,2-dimethoxyethane was added 8-chloromethyl-2,3-dimethylimidazo[1,2-a]pyridine (0.1 g, 0.51 mmol) in 1,2-dimethyxyethane (3 ml). The reaction mixture was stirred for 1.5 h. at room temperature and sodium iodide (0.035 g, 0.23 mmol) was added. The mixture was stirred for 3.5 h. and N,N-dimethylformamide (1 ml) and methanol were added and the solids were isolated by filtration. The filtrate was evaporated under reduced pressure, the residue was solved in methylene chloride and washed with saturated sodium bicarbonate. The organic layer was separated, dried and evaporated under reduced pressure. The residue was purified by column chromatography on silica gel using methylene chloride:methanol (100:3.5) as eluent to give 0.11 (78%) of the title compound.

$^1$H-NMR (400 MHz, CDCl$_3$): δ2.3 (s, 6H), 2.4 (s, 3H), 2.45 (s, 3H), 5.3 (s, 2H), 6.9 (t, 1H), 6.95 (t, 1H), 7.05 (d, 2H), 7.55 (d, 1H), 7.75 (d, 1H)

Example 1.77

Synthesis of 7-amino-2,3-dimethyl-8-(2,6-dimethylbenzylamino)-imidazo[1,2-a]pyridine A mixture of 2,3-dimethyl-8-(2,6-dimethylbenzylamino)-7-nitroimidazo[1,2-a]pyridine (45 mg, 0.139 mmol) Raney-Ni (0.1 g) and ethyl alcohol 4 ml was hydrogenated (H$_2$, 1 bar) at 40° C. for 3 h. The mixture was filtrated using a small amount of silica gel and the solvent was removed under reduced pressure. 40 mg (97%) of the title compound was obtained.

$^1$H-NMR (300 MHz, CDCl$_3$): δ2.30 (s, 3H), 2.34 (s, 3H), 2.49 (s, 6H), 3.85 (bs, 2H), 4.24 (s, 2H), 6.35 (d, 1H), 7.05–7.15 (m, 3H), 7.35 (d, 1H)

Example 1.78–1.79 were prepared according to Example 1.1

Example 1.78

Synthesis of 8-(2-methoxycarbonylamino-6-methylbenzylamino)-2,3,6-trimethylmethylimidazo[1,2-a]pyridine Yield: 37%

$^1$H-NMR (300 MHz, CDCl$_3$): δ2.35 (s, 9H), 2.4 (s, 3H), 3.7 (s, 3H), 4.35 (d, 2H), 4.75 (bs, 1H), 6.2 (s, 1H), 6.95 (d, 1H), 7.1 (s, 1H), 7.2 (m, 1H), 7.5 (bs, 1H), 7.7 (bs, 1H)

Example 1.79

Synthesis of 2,3-dimethyl-8-(4-trifluoromethoxybenzylamino)-imidazo[1,2-a]pyridine, hydrogen chloride Yield: 35%

2.3 (s, 3H), 2.4 (s, 3H), 4.4 (d, 2H), 5.65 (t, 1H), 5.95 (d, 1H), 6.55 (t, 1H), 7.05–7.2 (m, 3H), 7.35 (d, 2H)
Preparation of Intermediates Example 2.1

Synthesis of 2,6-dimethyl-4-fluorobenzylbromide

A mixture of 3,5-dimethyl-fluorobenzene (5 g, 0.04 mol), paraformaldehyde (15 g), hydrobromic acid (70 ml) (30% in acetic acid) and acetic acid (25 ml) was stirred at ambient temperature for 4.5 h. To the mixture, water and petroleum ether were added and the organic layer was separated dried over anhydrous sodium sulfate and evaporated carefully under reduced pressure. The residue was purified by column chromatography on silica gel with petroleum ether as eluent to give the desired product. (3.7 g, 43%).

$^1$H-NMR (300 MHz, CDCl$_3$): δ2.5 (s, 6H), 4.55 (s, 2H), 6.75 (d, 2H)

Example 2.2

Synthesis of 2-chloro-4,6-dimethylbenzylbromide

2-Chloro-3,5-dimethylbenzene (1.42 g, 0.01 mol) and paraformaldehyde (0.31 g, 0.01 mol) were added to 2 ml of hydrogenbromide (33%) in acetic acid. The mixture was stirred over night at +70° C. The reaction mixture was poured on 25 ml water and the product was extracted with diethyl ether. The organic layer was washed with water. The organic layer was dried (Na$_2$SO$_4$) and evaporated. 1.1 g product (oil) was obtained. The $^1$H-NMR spectrum shows that the substance was a mixture of the title compound and 4-chloro-2,6-dimethylbenzylbromide. The product was used as such without any further purification in the next synthetic step (Example 1.15).

$^1$H-NMR (300 MHz, CDCl$_3$): δ2.28 (s, 6H), 4.51 (s, 2H), 7.04 (s, 2H).

Example 2.3–2.4 were prepared according to example 2.1

Example 2.3

Synthesis of 2,4-dichloro-6-methylbenzylbromide

Yield: 0.7%

$^1$H-NMR (300 MHz, CDCl$_3$): δ2.43 (s, 3H), 4.61 (s, 2H), 7.11 (d, 1H), 7.27 (d, 1H)

Example 2.4

Synthesis of 4-fluoro-6-methyl-2-[2-(methylcarbonyloxy)ethyl]-benzylbromide

Yield: 31%

$^1$H-NMR (300 MHz, CDCl$_3$): δ2.12 (s, 3H), 2.32 (s, 3H), 2.88 (t, 2H), 4.26 (t, 2), 4.66 (s, 2H), 6.65–6.8 (m, 2H)

Example 2.5

Synthesis of 8-amino-2,3,6-trimethylimidazo[1,2-a]pyridine

To a solution of 2,3-diamino-5-methylpyridine (2.0 g, 16 mmol) in ethanol (100 ml) was added 3-bromo-2-butanon (2.4 g, 16 mmol). The reaction mixture was refluxed for 16 h. An additional amount of 3-bromo-2-butanon (1.0 g 6.7 mmol) and triethylamine (1.0 g, 9.9 mmol) were added and the mixture was refluxed for 2 h. The ethanol was evaporated under reduced pressure and the residue was treated with methylene chloride and a solution of bicarbonate. The organic layer was separated, dried over sodium sulfate and evaporated under reduced pressure. The oily residue was purified by column chromatography on silica gel, using methanol:methylene chloride (1: 20) as eluent to give the desired product (1.05 g, 37%).

$^1$H-NMR (300 MHz, DMSO-d$_6$): δ2.15 (s, 3H), 2.25 (s, 3H), 2.3 (s, 3H), 5.45 (bs, 2), 6.05 (s, 1H), 7.20 (s, 1H).

Example 2.6

Synthesis of 8-amino-3-carboethoxy-2,6-dimethylimidazo[1,2-a]pyridine

A stirred mixture of 2,3-diamino-5-methyl-pyridine (4.0 g, 32.5 mmol) and (5.9 g, 36.0 mmol) of ethyl-chloroacetoacetate in 75 ml abs. ethanol was refluxed over night. The ethanol was evaporated under reduced pressure. The residue was dissolved in 2 M HCl and washed 3 times with diethyl ether, pH was adjusted to 9 and extracted 3 times with dichloromethane. The organic layer was dried over anhydrous sodium sulfate and evaporated. The residue was purified by column chromatography on silica gel with dichloromethane:methanol 95:5 as eluent to give the title product 2.0 g (28%).

$^1$H-NMR (300 MHz, CDCl$_3$): δ1.42 (t, 3H), 2.28 (s, 3H), 2.65 (s, 3H), 4.40 (q, 2H), 4.47 (s, 2H), 6.40 (s, 1H), 8.55 (s, 1H).

Example 2.7

Synthesis of 3-carboethoxy-2,6-dimethyl-8-(2,6-dimethylbenzylamino) imidazo[1,2-a]pyridine A stirred mixture of 8-amino-2,6 dimethylimidazol [1,2-a]pyridine (1.2 g, 5.1 mmol), zinc(II)chloride (0.84 g, 6.2 mmol) and 2,6-dimethylbenzaldehyde (0.84 g, 6.2 mmol) in 50 ml methanol was treated with sodium cyanoborohydride (0.39 g, 6.2 mmol) and was refluxed for 5 h. The methanol was evaporated under reduced pressure and the residue was dissolved in dichloromethane and 40 ml 2 M sodium hydroxide. The organic layer was separated, dried over sodium sulfate and evaporated under reduced pressure. The residue was purified by column chromatography on silica gel, eluent petroleum ether (40–60): isopropyl ether 8:2, in yield of 0.8 g, (44%) of the title compound.

$^1$H-NMR (300 MHz, CDCl$_3$): δ1.44 (t, 3H), 2.35 (d, 9H), 2.60 (s, 3H), 4.33 (d, 2H), 4.40 (q, 2H), 4.6 (s, 1H), 6.60 (s, 1H), 7.10 (d, 2H), 7.25 (m, 1H), 8.50 (s, 1H).

Example 2.8

Synthesis of 3-carboethoxy-2,6-dimethyl-8-(2,6-dimethyl-4-fluorobenzylamino)-imidazo[1,2-a]pyridine A stirred mixture of (1.1 g, 4.7 mmol) 8-amino-3-carboethoxy-2,6-dimethylimidazo[1,2-a]pyridine (1.2 g, 5.7 mmol) 2,6-dimethyl-4-fluorobenzylbromide, (1.0 g, 7.5 mmol) potassium carbonate and (0.1 g) sodium iodide in 15 ml acetonitrile was refluxed over night. After evaporation of the solvent under reduced pressure the residue was dissolved in dichloromethane and washed with water, the organic layer was separated dried over sodium sulfate and evaporated under reduced pressure. The residue was purified by column chromatography on silica gel, eluent petroleum ether (40–60): isopropyl ether 7:3 to give 0.8 g, (47%) of the title compound.

$^1$H-NMR (300 MHz, CDCl$_3$): δ1.42 (t, 3H), 2.36 (s, 9H), 2.62 (2, 3H), 4.45 (d, 2H), 4.48 (q, 2H), 4.54 (s, 1H), 6.30, (s, 1H), 6.75 (d, 2H), 8.55 (s, 1H).

Example 2.9

Synthesis of 2,6-dimethyl-8-(2,6-dimethyl-4-fluorobenzylamino) imidazo[1,2- a]pyridine-3carboxylic acid A mixture of 3-carboethoxy-2,6-dimethyl-8-(2,6-dimethylbenzylamino) imidazo[1,2-a]pyridine (0.4 g, 1.1 mmol), sodium hydroxide (2M, 6 ml) and dioxane (6 ml) was refluxud for 20 min. The dioxane was removed under reduced pressure. pH was adjusted to pH=7 with 2M HCl and the formed precipitate was filtered off 0.23 g (75%) of the title compound was obtained.

Example 2.10 was prepared according to example 2.9.

Example 2.10

Synthesis of 2,6-dimethyl-8-(2,6-dimethylbenzylamino) imidazo[1,2- a]pyridine-3-carboxylic acid Yield: 100%

Example 2.11

Synthesis of ethyl 8-amino-3-methylimidazo[1,2-a] pyridine-2-carboxylate

A solution of 2,3-diaminopyridine (6.8 g, 62 mmol) and 3-bromo-2-oxo-butyric acid ethyl ester (13 g, 62 mmol) in 1,2-dimethoxyethane (150 ml) was refluxed for 2 h. Sodium carbonate (6.5 g, 62 mmol) was added and the mixture was refluxed for 2 h. The solids were isolated by filtration and washed with dichloromethane:methanol (10:1). The filtrate and washings were combined and the solvents were removed under reduced pressure. The oily residue was washed with petroleum ether and was purified twice by column chromatography on silica gel using 1) dichloromethane:methanol (10:1) 2) ethyl acetate as eluent to give 4.6 g (34%) of the title compound.

$^1$H-NMR (300 MHz, CDCl$_3$): δ1.45 (t, 3H), 2.75 (s, H), 4.5 (q, 2H), 4.65 (bs, 2H), 6.35 (d, 1H), 6.7 (t, 1H), 7.35 (d, 1H)

Example 2.12

Synthesis of ethyl 8-(2,6-dimethylbenzylamino)-3-methylimidazo[1,2-a]pyridine-2-carboxylate Ethyl 8-amino-3-methylimidazo[1,2-a]pyridine-2-carboxylate (4.6 g, 21 mmol), 2,6-dimethylbenzyl chloride (3.2 g, 21 mmol), sodium carbonate (4.4 g, 42 mmol) and a cat. amount of potassium iodide were added to acetonitrile (50 ml) and refluxed for 3 h. stirred for 20 h. at room temperature and refluxed for 1 h. The solids were removed by filtration and the solvents were evaporated under reduced pressure. The residue was dissolved in methylene chloride and washed with water. The organic layer was separated, dried (Na$_2$SO$_4$) and evaporated under reduced pressure. Purification of the residue by column chromatography on silica gel using methylene chloride:methanol (10:1) as eluent and crystallization from ethyl acetate gave 4.0 g (56%) of the desired product.

$^1$H-NMR (300 MHz, CDCl$_3$): δ1.4 (t, 3H), 2.4 (s, 6H), 2.75 (s, 3H), 4.35 (d, 2H), 4.45 (q, 2H), 5.15 (t, 1H), 6.25 (d, 1H), 6.85 (t, 1H), 7.05–7.2 (m, 3H), 7.35 (d, 1H)

Example 2.13

Synthesis of 8-(2,6-dimethylbenzylamino)-2-hydroxymethyl-3-methylimidazo[1,2-a]pyridine Ethyl 8-(2,6-dimethylbenzylamino)-3-methylimidazo[1,2-a]pyridine-2-carboxylate (5.2 g, 0.015 mol) was solved in tetrahydrofuran (100 ml) and LiAlH4 (1.15 g 0.03 mol) was added. After stirring the mixture at room temperature, for 45 min, 1.15 ml of water was added dropwise, followed by 1.15 ml of 15% sodium hydroxide and then 3.45 ml of water. The solids were removed by filtration and washed thoroughly with methylene chloride. The filtrate and washings were combined and dried and the solvents were removed under reduced pressure. Purification of the residue by column chromatography on silica gel using methylene chloride methanol (10:2) as eluent gave 3.2 g (73%) of the title compound.

$^1$H-NMR (300 MHz, DMSO-d6): δ2.35 (s, 6H), 2.4 (s, 3H), 4.35 (d, 2H), 4.5 (d, 2H), 4.85 (t, 1H), 4.9 (t, 1H), 6.3 (s, 1H), 6.8 (t, 1H), 7.05–7.2 (m, 3H), 7.55 (d, 1H)

Example 2.14

Synthesis of 8-(2,6-dimethylbenzylamino)-2-chloromethyl-3-methylimidazo[1,2-a]pyridine To a solution of 8-(2,6-dimethylbenzylamino)-2-hydroxymethyl-3-methylimidazo[1,2-a]pyridine (1.0 g, 3.4 mmol) in methylene chloride (50 ml) was added dropwise thionyl chloride (0.5 g, 3.4 mmol) solved in methylene chloride (10 ml) at 5° C. The reaction mixture was stirred 2 h. at 5° C. To the mixture was washed with a saturated bicarbonate solution, the organic layer was separated, dried (Na$_2$SO$_4$) and evaporated under reduced pressure to give 1.0 g (93%) of the title compound.

$^1$H-NMR (300 MHz, CDCl$_3$): δ2.4 (s, 6H), 2.5 (s, 3H), 4.35 (d, 2H), 4.75 (s, 2H), 4.9 (bs, 1H), 6.25 (d, 1H), 6.8 (t, 1H), 7.05–7.15 (m, 3H), 7.25 (d, 1H)

Example 2.15

Synthesis of 2,3-dimethyl-8-(2,6-dimethylbenzylamino)imidazo[1,2-a]pyridine

A mixture of 8-amino-2,3-dimethylimidazo[1,2-a]pyridine (0.7 g, 4.34 mmol), sodium carbonate (2.0 g), sodium iodide (0.3 g), 2,6-dimethylbenzylchloride (0.671 g, 4.34 mmol) and acetone (30 ml) was stirred overnight. The reaction mixture was filtered and the solvent was removed in vacuo. The residue was dissolved in methylene chloride and washed with aqueous NaHCO$_3$. The organic layer was separated and the solvent was evaporated. The crude product was purified by flash chromatography eluting with CH$_2$Cl$_2$/MeOH to give 0.7 g of the title compound.

$^1$H NMR (300 MHz, CDCl$_3$): δ7.25 (d, J=7.7 Hz, 1H), 7.14–7.09 (m, 1H), 7.03 (d, J=7.7 Hz, 2H), 6.73 (t, J=7.7 Hz, 1H), 6.21 (d, J=7.7 Hz, 1H), 4.79 (br "t", 1H), 4.34 (d, J=4.5 Hz, 2H), 2.38 (s, 6H), 2.34 (s, 6H).

Example 2.16

Synthesis of 8-amino-3-acetyl-2-methylimidazo[1,2-a]pyridine

A mixture of 2,3-diaminopyridine (7 g, 64.1 mmol), 3-chloroacetylacetone (8.6 g, 64.1 mmol) in ethyl alcohol (80 ml) was refluxed for 9 hours. The solvent was removed under reduced pressure and the residue dissolved in methylene chloride. A sodium bicarbonate solution was added and the organic layer was separated. The aqueous layer was extracted twice with methylene chloride. The combined organic layer was dried and evaporated under reduced pressure. Chromatography of the residue on silica gel (methylene chloride:methanol, 100:5) gave a product which after recrystallisation from ethyl acetate gave 1.9 g (15%) of the title compound.

$^1$H NMR (300 MHz, CDCl$_3$): δ2.6 (s, 31H), 2.75 (s, 31H), 4.5 (bs, 2H), 6.6 (d, 1H), 6.8 (t, 1H), 9.15 (t, 1H)

Example 2.17 was prepared according to example 1.1

Example 2.17

Synthesis of 3-acetyl-8-(2,6-dimethylbenzylamino)-2-methylimidazo[1,2-a]pyridine Yield: 72%

1H NMR (300 MHz, CDCl$_3$): δ2.4 (s, 6H), 2.6 (s, 3H), 2,7 (s, 3H), 4.35 (d, 2H), 4.85 (bs, 1H), 6.55 (d, 1H), 7.9 (t, 1H), 7.0–7.2 (m, 31H), 9.1 (d, 1H)

Example 2.18

Synthesis of 1-[8-(2,3-dimethylbenzylamino)-2-methylimidazo[1,2-a]pyridine-3-yl]-1-ethanol To a mixture of 3-acetyl-8-(2,6-dimethylbenzylamino)-2-methylimidazo[1,2-a]pyridine (500 mg, 1.63 mmol) and methanol (20 ml) was sodium borohydride (62 mg, 1.63 mmol) added in portions. Tetrahydrofuran was added and the mixture stirred for 1 hour. TLC showed starting material and sodium borohydride (62 mg, 1.63 mmol) was added and the mixture stirred for 1.5 hour. The solvent was removed under reduced pressure and to the residue, methylene chloride and water was added. pH was adjusted to pH=3 with hydrogen chloride (conc.) and thereafter alkaline with sodium bicarbonate. The methylene choride layer was separated washed with water, dried over sodium sulfate and evaporated in vacuo. The residue was treated with ethanol/ethyl acetate and after filtration (410 mg, 81%).

$^1$H NMR (300 MHz, CDCl$_3$): δ1.6 (d, 3H), 2.15 (s, 3H), 2.4 (s,3H), 4.35 (d, 2H), 4.8 (bs, 1H), 5.2 (q, 1H), 6.25 (d, 1H), 6.7 (t,1H), 7.0–7.2 (m, 3H), 6.8 (d, 1H)

Example 2.19 and 2.20

Synthesis of 2-chloro-6-methylbenylbromide and 3 chloro-2-methylbenzylbromide

A mixture of 3-chloro-o-xylene (20 g, 142.2 mmol), N-bromo succinimid (26.57 g, 149.3 mmol), dibenzoylperoxid (0.67 g) and tetrachloromethane (200 ml) was refluxed for 5 hours. After filtration the filtrate was washed with sodium hydrogensulfite and water. The organic layer was dried over sodium sulfate and evaporated in vacuo. Chromatography (SiO2) (petroleum ether:ethyl acetate, 100:4) gave a 10 g fraction containing a mixture of the two title compounds 2-chloro-6-methylbenzylbromide (2.19): 3-chloro-2-methylbenzylbromide (2.20), 1:0.7. This mixture was used without further purification.

Example 2.21 was prepared according to example 2.8

Example 2.21

Synthesis of ethyl 8-(2,6-dimethylbenzylamino)-2-methylimidazo[1,2-a]pyridine-3-carboxylate Yield: 34%

$^1$H NMR (300 MHz, CDCl$_3$): δ1.4 (t,3H), 2.35 (s, 3H), 2.45 (s, 3H), 2.6 (s, 3H), 4.4 (q, 2H), 4.5 (d, 2H), 4.9 (bs, 1H), 6.35 (s, 1H), 7.05–7.35 (m, 3H), 8.5 (s, 1H)

Example 2.22, 2.23 (mixture), 2.24, 2.25 and 2.26 were prepared according to example 2.19 and 2.20.

Example 2.22 and 2.23

Synthesis of 2-bromo-6-methylbenzylbromide (2.22) and 3-bromo-2-methylbenzylbromide (2.23)

Yield: 78% (16.8 g of a fraction containing a mixture of the two title compounds (2.22:2.23), 1:0.7)

Example 2.24

Synthesis of ethyl 2-bromomethyl-3-methylbenzoate

Yield: 26%

$^1$H NMR (300 MHz, CDCl$_3$): δ1.4 (t, 3H), 2.45 (s, 3H), 4.4 (q, 2H), 5.0 (s, 2H), 7.2–7.4 (m, 2H) 7.75 (d, 1H)

Example 2.25 and 2.26

Synthesis of 2-bromomethyl-3-methylbenzonitrile (2.25) and 3-bromomethyl-2-methylbenzonitrile (2.26)

Yield: 5.6% (2.25)

18% (7.6 g of fraction containing a mixture of the two compounds (2.25:2.26), 1.8:1)

$^1$H NMR (300 MHz, CDCl$_3$) Example 2.25: δ2.45 (s, 3H), 4.70 (s, 2H), 7.2–7.6 (m, 3H)

Example 2.27

Synthesis of 2-(2,3-dimethylimidazo[1,2-a]pyridin-8-yl)-4-methyl-1-isoindoline

The title compound was obtained in the synthesis of example 1.15 (8-(2-ethoxycarbonyl-6-methylbenzylamino)-2,3-dimethyl imidazo[1,2-a]pyridine).

Yield: 24%

$^1$H NMR (300 MHz, CDCl$_3$): δ2.91 (s, 3H), 2.92 (s, 3H), 2.94 (s, 3H), 5.4 (s, 2H), 6.9 (t, 1H), 7.35–7.45 (m, 2H), 7.65 (d, 1H), 7.7–7.85 (m, 2H)

Example 2.28

Synthesis of 2-(((2,3-dimethylimidazo[1,2-a]pyridin-8-yl)amino)methyl)-3-methylbenzoic acid A mixture of Example 2.27 (700 mg. 2.4 mmol), sodiumhydroxide (15 ml, 10M) and ethyl alcohol (30 ml) and water (7.5 ml) was refluxed for 4 days. The organic solvent was evaporated in vacuo. The residue was partitioned between methylene chloride and water. The aqueous layer was cooled and hydrogen chloride (conc.) was added. After extraction with methylene chloride, a mixture of the title compound and Example 2.27 (150 mg) was obtained. The product crystallize from ethyl alcohol and after filtration the precipitate was washed with ethyl alcohol and methylene chloride. 60 mg (8%) of the title compound was obtained.

$^1$H NMR (300 MHz, CD$_3$OD): δ2.35 (s, 3H), 2.45 (s, 3H), 2.47 (s, 3H), 4.65 (s, 2H), 6.95 (d, 1H), 7.2–7.45 (m, 3H), 7.6 (d, 1H), 7.8 (d, 1H)

Example 2.29

Synthesis of 2-bromo-1-methoxymethyl-3-methylbenzene

To a stirred solution of 2-bromo-3-methylbenzylbromide (5.2 g, 0.0197 mol) in methanol (30 ml) was added saturated sodiumbicarbonate (5 ml) and the mixture was refluxed overnight. The mixture was neutralised with acetic acid and the solvent was evaporated under reduced pressure. Chromatography of the residue on silica gel using hexane:methylene chloride (7/3) as eluent gave 4.2 g (99%) of the title compound.

$^1$ H-NMR (300 MHz, CDCl$_3$): δ2.43 (s, 3H), 3.47 (s, 3H), 4.55 (s, 2H), 7.18–7.30 (m, 3H)

Example 2.30 was prepared according to Example 2.29

Example 2.30

Synthesis of 2-bromo-1,3-bis(methoxymethyl)benzene

Yield: 94%

$^1$H-NMR (500 MHz, CDCl$_3$): δ3.5 (s, 6H), 4.6 (2, 4H), 7.35–7.45 (m, 3H)

Example 2.31

Synthesis of 2-bromo-3-methylbenzylcyanid

A mixture of 2-bromo-3-methylbenzylbromide (25 g, 0.095 mol) and potassium cyanide (16 g, 0.25 mol) in dimethylformamide (100 ml) was stirred at 90° C. for 20 h. The solvent was evaporated under reduced pressure and to the residue were added toluene and water. The organic layer was separated washed with water, separated and evaporated under reduced pressure. Purification of the residue by column chromatography on silica gel using methylene chloride as eluent gave 8.8 g (44%) of the title compound.

$^1$H-NMR (300 MHz, CDCl$_3$): δ2.42 (s, 3H), 3.83 (s, 2H), 7.21–7.35 (m, 3H)

Example 2.32

Synthesis of 2-bromo-3-methylphenyl Acetic Acid 2-bromo-3-methylbenzylcyanid (8.8 g, 42 mmol) was added to a mixture of conc sulfuric acid (50 ml) and water (60 ml) and was refluxed overnight. Water (150 ml) and diethyl ether were added and the organic layer was separated. To the organic layer was added a saturated sodium bicarbonate solution and the aqueous layer was separated. The aqueous layer was made acidic by addition of conc sulfuric acid. The acidic water solution was extracted with diethyl ether and the organic layer was washed with water, dried (Na$_2$SO$_4$) and evaporated under reduced pressure to give 6.5 g of the title compound.

$^1$H-NMR (300 MHz, CDCl$_3$): δ2.43 (s, 3H), 3.87 (s, 3H), 7.1–7.2 (m, 3H)

Example 2.33

Synthesis of ethyl 2-bromo-methylphenyl Acetate

To a stirred mixture of 2-bromo-3-methylphenyl acetic acid (4.8 g, 21 mmol) in ethanol (50 ml) was added a small amount of conc. sulfuric acid and the mixture was refluxed overnight. Sodium carbonate (1 g) was added and the solvent was evaporated under reduced pressure. To the residue were added methylene chloride and water. The organic layer was separated and evaporated under reduced pressure. Purification of the residue by column chromatography on silica gel using methylene chloride as eluent gave 2.0 a (37%) of the desired product as an oil.

$^1$H-NMR (300 MHz, CDCl$_3$): δ1.27 (t, 3H), 2.43 (s, 3H), 3.81 (s, 2H), 4.18 (q, 2H), 7.2–7.4 (m, 3H)

Example 2.34

Synthesis of 2-(2-bromo-3-methylphenyl)ethanol

To a stirred solution of 2-bromo-methylphenyl acetate (2 g, 7.9 mmol) in tetrahydrofuran (30 ml) was added LiAlH$_4$ (0.8 g, 21 mmol) at 0–5° C. After stirring the mixture at 0–5° C. for 2 h., 0.8 ml of water was added dropwise, followed by 0.8 ml of 15% sodium hydroxide and then 2.4 ml of water. The solids were removed by filtration and washed with tetrahydrofuran and tetrahydrofuran/methanol (9/1). The filtrate and washings were combined and the solvents were removed under reduced pressure. The residue was solved in methylene chloride/methanol (9/1) and was filtrated through silica gel (0.5 g). The solvent was evaporated under reduced pressure to give 1.6 g (95%) of the title compound.

$^1$H-NMR (300 MHz, CDCl$_3$): δ2.43 (s, 3H), 3.07 (t, 2H), 3.89 (t, 2H), 7.1–7.3 (m, 3H)

Example 2.35

Synthesis of 2-(2-bromo-3-methylphenyl)ethyl methylether

To a stirred solution of 2-(2-bromo-3-methylphenyl)ethanol (1.6 g, 7.4 mmol) in tetrahydrofuran (20 ml) was added sodium hydride (50% in oil) (0.46 g, 9.6 mmol). After stirring the mixture for 15 min methyl iodide (1.6 g, 11.3 mmol) was added and the reaction mixture was stirred for 3 h. at room temperature. Water (0.2 g) was added and then acetic acid (0.2 g). The solvents were evaporated under reduced pressure and purification of the residue by column chromatography on silica gel using methylene chloride as eluent gave 1.5 g (89%) of the desired product as an oil.

$^1$H-NMR (300 MHz, CDCl$_3$): δ2.42 (s, 3H), 3.07 (t, 2H), 3.38 (s, 3H), 3.62 (t, 2H), 7.1–7.25 (m, 3H)

Example 2.36

Synthesis of 2-(2-methoxyethyl)-6-methylbenzaldehyd

To a stirred solution of 2-(2-bromo-3-methylphenyl)ethyl methylether (1.5 g, 6.5 mmol) in anhydrous tetrahydrofuran (10 ml) was added magnesium (turnings) (0.16 g, 6.6 mmol). The mixture was refluxed in a nitrogen atmosphere until the reaction started and then stirred without heating for 15 min. The mixture was stirred at 50° C. overnight. The mixture was cooled to room temperature and N,N-dimethylformamide (0.7 g) was added and the mixture was stirred for 30 min. A saturated ammonium chloride solution (10 ml) was added and the mixture was stirred for 1 h. at room temperature. Toluene (20 ml) was added and the organic layer was separated, dried (Na$_2$SO$_4$) and evaporated under reduced pressure. The residue was purified by column chromatography on silica gel using methylene chloride as eluent to separate the lipophilic biproducts and methylene chloride/diethyl ether(7:3) as eluent to isolate (0.17 g, (15%) of the title compound as an oil.

$^1$H-NMR (300 MHz, CDCl$_3$): δ2.61 (s, 3H), 3.25 (t, 2H), 3.36 (s, 3H), 3.61 (t, 2H), 7.1–7.4 (m, 3H)

Example 2.37, 2.38 and 2.39 were prepared according to Example 2.36

Example 2.37

Synthesis of 2-methoxymethyl-6-methylbenzaldehyd

Yield: 90%

$^1$H-NMR (300 MHz, CDCl$_3$): δ2.64 (s, 3H), 3.43 (s, 3H), 4.78 (s, 2H), 7.2–7.45 (m, 3H), 10.55 (s, 1H)

Example 2.38

Synthesis of 2,6-bis(methoxymethyl)-benzaldehyd

Yield: 79%

$^1$H-NMR (500 MHz, CDCl$_3$): δ3.5 (s, 6H), 4.85 (s, 4H), 7.6 (s, 3H), 10.55 (s, 1H)

Example 2.39

Synthesis of 2,5-dimethylthiophene-3-carbaldehyde

Yield: 57%

$^1$H-NMR (300 MHz, CDCl$_3$): δ2.41 (s, 3H), 2.74 (s, 3H), 6.62 (s, 1H), 10.11 (s, 1H)

Biological Tests

1. In vitro Experiments

Acid Secretion Inhibition in Isolated Rabbit Gastric Glands

Inhibiting effect on acid secretion in vitro in isolated rabbit gastric glands was measured as described by Berglindh et al. (1976) Acta Physiol. Scand. 97, 401–414.

Determination of H$^+$, K$^+$-ATPase Activity

Membrane vesicles (2.5 to 5 μg) were incubated for 15 min at +37° C. in 18 mM Pipes/Tris buffer pH 7.4 containing 2 mM MgCl$_2$, 10 mM KCl and 2 mM ATP. The ATPase activity was estimated as release of inorganic phosphate from ATP, as described by LeBel et al. (1978) Anal. Biochem. 85, 86–89.

2. In vivo Experiments

Inhibiting Effect on Acid Secretion in Female Rats

Female rats of the Sprague-Dawly strain are used. They are equipped with cannulated fistulae in the stomach (lumen) and the upper part of the duodenum, for collection of gastric secretions and administration of test substances, respectively. A recovery period of 14 days after surgery is allowed before testing commenced.

Before secretory tests, the animals are deprived of food but not water for 20 h. The stomach is repeatedly washed through the gastric cannula with tap water (+37° C.), and 6 ml Ringer-Glucose given subcutaneously. Acid secretion is stimulated with infusion during 2.5–4 h (1.2 ml/h, subcutaneously) of pentagastrin and carbachol (20 and 1 10 nmol/kg·h, respectively), during which time gastric secretions are collected in 30-min fractions. Test substances or vehicle are given either at 60 min after starting the stimulation (intravenous and intraduodenal dosing, 1 ml/kg), or 2 h before starting the stimulation (oral dosing, 5 ml/kg, gastric cannula closed). The time interval between dosing and stimulation may be increased in order to study the duration of action. Gastric juice samples are titrated to pH 7.0 with NaOH, 0.1 M, and acid output calculated as the product of titrant volume and concentration.

Further calculations are based on group mean responses from 4–6 rats. In the case of administration during stimulation; the acid output during the periods after administration of test substance or vehicle are expressed as fractional responses, setting the acid output in the 30-min period preceding administration to 1.0. Percentage inhibition is calculated from the fractional responses elicited by test compound and vehicle. In the case of administration before stimulation; percentage inhibition is calculated directly from acid output recorded after test compound and vehicle.

Bioavailability in Rat

Adult rats of the Sprague-Dawley strain are used. One to three days prior to the experiments all rats are prepared by cannulation of the left carotid artery under anaesthesia. The rats used for intravenous experiments are also cannulated in the jugular vein (Popovic (1960) J. Appl. Physiol. 15, 727–728). The cannulas are exteriorized at the nape of the neck.

Blood samples (0.1–0.4 g) are drawn repeatedly from the carotid artery at intervals up to 5.5 hours after given dose. The samples are frozen until analysis of the test compound.

Bioavailability is assessed by calculating the quotient between the area under blood/plasma concentration (AUC) curve following (i) intraduodenal (i.d.) or oral (p.o.) administration and (ii) intravenous (i.v.) administration from the rat or the dog, respectively.

The area under the blood concentration vs. time curve, AUC, is determined by the log/linear trapezoidal rule and extrapolated to infinity by dividing the last determined blood concentration by the elimination rate constant in the terminal phase. The systemic bioavailability (F%) following intraduodenal or oral administration is calculated as F(%)= (AUC (p.o. or i.d.)/AUC (i.v.))×100.

Inhibition of Gastric Acid Secretion and Bioavailability in the Conscious Dog

Labrador retriever or Harrier dogs of either sex are used. They are equipped with a duodenal fistula for the administration of test compounds or vehicle and a cannulated gastric fistula or a Heidenhaim-pouch for the collection of gastric secretion.

Before secretory tests the animals are fasted for about 18 h but water is freely allowed. Gastric acid secretion is stimulated for up to 6.5 h infusion of histamine dihydrochloride (12 ml/h) at a dose producing about 80% of the individual maximal secretory response, and gastric juice collected in consecutive 30-min fractions. Test substance or vehicle is given orally, i.d. or i.v., 1 or 1.5 h after starting the histamine infusion, in a volume of 0.5 ml/kg body weight. In the case of oral administration, it should be pointed out that the test compound is administered to the acid secreting main stomach of the Heidenham-pouch dog.

The acidity of the gastric juice samples are determined by titration to pH 7.0, and the acid output calculated. The acid output in the collection periods after administration of test substance or vehicle are expressed as fractional responses, setting the acid output in the fraction preceding administration to 1.0. Percentage inhibition is calculated from fractional responses elicited by test compound and vehicle.

Blood samples for the analysis of test compound concentration in plasma are taken at intervals up to 4 h after dosing. Plasma is separated and frozen within 30 min after collection and later analyzed. The systemic bioavailability (F%) after oral or i.d. administration is calculated as described above in the rat model.

What is claimed is:

1. A compound of the formula I, (I)

[Structure of Formula I]

or a pharmaceutically acceptable salt thereof, wherein:

X is

[Structure showing $R^8$-CH-O or $R^8$-CH-NH]

$R^1$ is $CH_3$;

$R^2$ is $CH_3$;

$R^3$ is $C_1$–$C_6$ alkoxycarbonyl;

$R^4$ is H;

Ar is a phenyl group; and $R^8$ is H.

2. A compound according to claim 1, or a pharmaceutically acceptable salt thereof, wherein $R^3$ is C=OOCH$_3$ or C=OOCH$_2$CH$_3$.

3. A process for the preparation of a compound according to any one of claims 1 or 2, comprising:
reacting a compound of Formula II, (II)

[Structure of Formula II]

wherein $X^1$ is $NH_2$ or OH, and $R^1$, $R^2$, $R^3$, and $R^4$ are as defined in claim 1, with a compound of Formula III, (III)

[Structure of Formula III]

wherein Ar is as defined in claim 1 and Y is a leaving group, in an inert solvent, and optionally in the presence of a base, to give a compound of Formula I.

4. A process for the preparation of a compound according to any one of claims 1 or 2, wherein X is $NHCH_2$, comprising:

a) reacting a compound of Formula IV, (IV)

[Structure of Formula IV]

wherein $R^1$, $R^2$, $R^3$ and $R^4$ are as defined in claim 1, with a compound of Formula V, (V)

[Structure of Formula V]

wherein Ar is as defined in claim 1, in an inert solvent in the presence of a Lewis acid under standard conditions to give a compound of formula VI, (VI)

[Structure of Formula VI]

wherein $R^1$, $R^2$, $R^3$, $R^4$ and Ar are as defined in claim 1; and b) treating the compound of Formula VI, wherein $R^1$, $R^2$, $R^3$, $R^4$ and Ar are as defined in claim 1, with sodium borohydride or sodium cyanoborohydride under standard conditions in a solvent, to give a compound of Formula I, wherein X is $NHCH_2$.

5. A process for the preparation of a compound according to any one of claims 1 or 2, wherein X is $CH_2O$, comprising:

a) reacting a compound of Formula XII

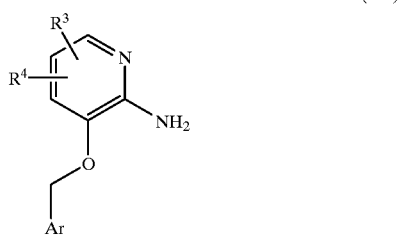

(XII)

with an α-halocarbonyl compound of formula $R^2COCH(Z)R^1$ wherein $R^1$ and $R^2$ are as defined in claim 1 and Z is a leaving group, in an inert solvent under standard conditions, to give a compound of Formula XIII,

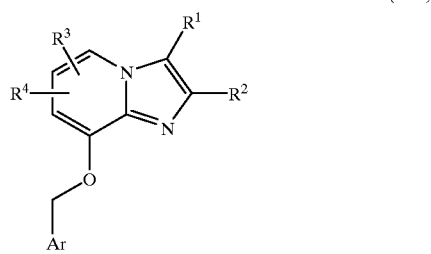

(XIII)

wherein $R^1$, $R^2$, $R^3$, $R^4$, and Ar are as defined in claim 1.

6. A pharmaceutical formulation containing a compound according to any one of claims 1 or 2 as active ingredient in combination with a pharmaceutically acceptable diluent or carrier.

7. A method for inhibiting gastric acid secretion which comprises administering to a mammal in need of such inhibition an effective amount of a compound according to any one of claims 1 or 2.

8. A method for the treatment of gastrointestinal inflammatory diseases which comprises administering to a mammal in need of such treatment an effective amount of a compound according to any one of claims 1 or 2.

9. A method for the treatment or prophylaxis of conditions involving infection by *Helicobacter pylori* of human gastric mucosa, which comprises administering to a mammal in need of such treatment an effective amount of a compound as claimed in any one of claims 1 or 2 in combination with at least one antimicrobial agent.

10. The process of claim 3, wherein the leaving group Y is selected from the group consisting of halide, tosyloxy, and mesyloxy.

11. The process of claim 3, wherein the inert solvent is selected from the group consisting of acetone, acetonitrile, dimethoxyethane, methanol, ethanol, and N,N-dimethylformamide.

12. The process of claim 3, wherein the base is selected from the group consisting of alkali metal hydroxides, alkali metal carbonates, and organic amines.

13. The process of claim 4, wherein the Lewis acid is zinc chloride.

14. The process according to claim 4, wherein the solvent in b) is selected from the group consisting of methanol and ethanol.

15. The process of claim 5, wherein the leaving, group Z is selected from the group consisting of Br and Cl.

16. The process of claim 5, wherein the inert solvent is selected from the group consisting of acetonitrile and ethanol.

17. The pharmaceutical formulation of claim 6 further comprising at least one antimicrobial agent.

* * * * *